(12) United States Patent
Frisén et al.

(10) Patent No.: US 10,774,374 B2
(45) Date of Patent: Sep. 15, 2020

(54) SPATIALLY DISTINGUISHED, MULTIPLEX NUCLEIC ACID ANALYSIS OF BIOLOGICAL SPECIMENS

(71) Applicants: Spatial Transcriptomics AB, Solna (SE); ILLUMINA, INC., San Diego, CA (US)

(72) Inventors: Jonas Frisén, Stockholm (SE); Patrik Ståhl, Stockholm (SE); Joakim Lundeberg, Lidingö (SE); Gordon M. Cann, San Diego, CA (US); Leila Bazargan, San Francisco, CA (US); Alex Aravanis, San Diego, CA (US)

(73) Assignee: Spatial Transcriptomics AB and Illumina, Inc., San Diego, CA (US)

( * ) Notice: Subject to any disclaimer, the term of this patent is extended or adjusted under 35 U.S.C. 154(b) by 0 days.

(21) Appl. No.: 15/565,637

(22) PCT Filed: Apr. 4, 2016

(86) PCT No.: PCT/EP2016/057355
§ 371 (c)(1),
(2) Date: Nov. 15, 2018

(87) PCT Pub. No.: WO2016/162309
PCT Pub. Date: Oct. 13, 2016

(65) Prior Publication Data
US 2019/0203275 A1    Jul. 4, 2019

Related U.S. Application Data

(60) Provisional application No. 62/145,874, filed on Apr. 10, 2015.

(51) Int. Cl.
C12Q 1/68       (2018.01)
C12Q 1/6834    (2018.01)
(Continued)

(52) U.S. Cl.
CPC ......... *C12Q 1/6834* (2013.01); *C12Q 1/6841* (2013.01); *C12Q 1/6874* (2013.01); *C12Q 1/6876* (2013.01)

(58) Field of Classification Search
CPC .. C12Q 1/6834; C12Q 1/6841; C12Q 1/6874; C12Q 1/6876; C12Q 2543/101;
(Continued)

(56) References Cited

U.S. PATENT DOCUMENTS 4,683,195 A    7/1987  Mullis
4,883,867 A   11/1989  Lee
(Continued)

FOREIGN PATENT DOCUMENTS

EP    1910562    4/2008
EP    1923471    5/2008
(Continued)

OTHER PUBLICATIONS

Affymetrix, "GeneChip Human Genome U133 Set," retrieved from the Internet: on the World Wide Web at affymetrix.com/support/technical/datasheet/hgu133_datasheet.pdf, retrieved on Feb. 26, 2003.
(Continued)

*Primary Examiner* — Betty J Forman
(74) *Attorney, Agent, or Firm* — Fish & Richardson P.C.

(57) ABSTRACT

A method for spatially tagging nucleic acids of a biological specimen, including steps of (a) providing a solid support comprising different nucleic acid probes that are randomly located on the solid support, wherein the different nucleic acid probes each includes a barcode sequence that differs from the barcode sequence of other randomly located probes on the solid support; (b) performing a nucleic acid detection reaction on the solid support to locate the barcode sequences on the solid support; (c) contacting a biological specimen with the solid support that has the randomly located probes;
(Continued)

(d) hybridizing the randomly located probes to target nucleic acids from portions of the biological specimen; and (e) modifying the randomly located probes that are hybridized to the target nucleic acids, thereby producing modified probes that include the barcode sequences and a target specific modification, thereby spatially tagging the nucleic acids of the biological specimen.

22 Claims, 8 Drawing Sheets

(51) Int. Cl.
  *C12Q 1/6841* (2018.01)
  *C12Q 1/6874* (2018.01)
  *C12Q 1/6876* (2018.01)

(58) Field of Classification Search
  CPC ........ C12Q 2565/514; C12Q 2565/537; C12Q 1/6837; C12Q 2525/161; C12Q 2565/543; B01J 2219/00596; G01N 33/50; G01N 33/543; C12N 15/1065
  See application file for complete search history.

(56) References Cited

U.S. PATENT DOCUMENTS

| | | |
|---|---|---|
| 5,002,882 A | 3/1991 | Lunnen |
| 5,308,751 A | 5/1994 | Ohkawa |
| 5,455,166 A | 10/1995 | Walker |
| 5,503,980 A | 4/1996 | Cantor |
| 5,512,439 A | 4/1996 | Hornes |
| 5,512,462 A | 4/1996 | Cheng |
| 5,559,032 A | 9/1996 | Pomeroy |
| 5,599,675 A | 2/1997 | Brenner |
| 5,641,658 A | 6/1997 | Adams |
| 5,716,825 A | 2/1998 | Hancock et al. |
| 5,750,341 A | 5/1998 | Macevicz |
| 5,763,175 A | 6/1998 | Brenner |
| 5,912,148 A | 6/1999 | Eggerding |
| 6,013,440 A | 1/2000 | Lipshutz |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,210,891 B1 | 4/2001 | Nyren |
| 6,210,894 B1 | 4/2001 | Brennan |
| 6,214,587 B1 | 4/2001 | Dattagupta |
| 6,258,558 B1 | 7/2001 | Szostak |
| 6,258,568 B1 | 7/2001 | Nyren |
| 6,266,459 B1 | 7/2001 | Walt |
| 6,281,804 B1 | 8/2001 | Haller |
| 6,309,824 B1 | 10/2001 | Drmanac |
| 6,344,316 B1 | 2/2002 | Lockhart |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,416,950 B1 | 7/2002 | Lohse |
| 6,432,360 B1 | 8/2002 | Church et al. |
| 6,485,982 B1 | 11/2002 | Charlton |
| 6,544,732 B1 | 4/2003 | Chee |
| 6,579,695 B1 | 6/2003 | Lambalot |
| 6,620,584 B1 | 9/2003 | Chee |
| 6,632,641 B1 | 10/2003 | Brennan |
| 6,673,620 B1 | 1/2004 | Loeffler |
| 6,699,710 B1 | 3/2004 | Kononen |
| 6,770,441 B2 | 8/2004 | Dickinson |
| 6,773,886 B2 | 8/2004 | Kaufman |
| 6,787,308 B2 | 9/2004 | Balasubramanian |
| 6,800,453 B2 | 10/2004 | Labaer |
| 6,828,100 B1 | 12/2004 | Ronaghi |
| 6,833,246 B2 | 12/2004 | Balasubramanian |
| 6,878,515 B1 | 4/2005 | Landegren |
| 6,890,741 B2 | 5/2005 | Fan et al. |
| 6,897,023 B2 | 5/2005 | Fu |
| 6,911,345 B2 | 6/2005 | Quake |
| 6,913,921 B2 | 7/2005 | Fischer |
| 6,969,488 B2 | 11/2005 | Bridgham |
| 6,969,589 B2 | 11/2005 | Patil |
| 6,977,033 B2 | 12/2005 | Becker |
| 7,052,244 B2 | 5/2006 | Fouillet |
| 7,057,026 B2 | 6/2006 | Barnes |
| 7,115,400 B1 | 10/2006 | Adessi |
| 7,118,883 B2 | 10/2006 | Inoue |
| 7,163,612 B2 | 1/2007 | Sterling |
| 7,211,414 B2 | 5/2007 | Hardin |
| 7,229,769 B2 | 6/2007 | Kozlov |
| 7,255,994 B2 | 8/2007 | Lao |
| 7,264,929 B2 | 9/2007 | Rothberg |
| 7,297,518 B2 | 11/2007 | Quake |
| 7,315,019 B2 | 1/2008 | Turner |
| 7,329,492 B2 | 2/2008 | Hardin |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,537,897 B2 | 5/2009 | Brenner |
| 7,544,473 B2 | 6/2009 | Brennan |
| 7,579,153 B2 | 8/2009 | Brenner |
| 7,595,883 B1 | 9/2009 | El Gamal |
| 7,601,492 B2 | 10/2009 | Fu et al. |
| 7,601,498 B2 | 10/2009 | Mao |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,754,429 B2 | 7/2010 | Rigatti |
| 7,858,321 B2 | 12/2010 | Glezer |
| 7,955,794 B2 | 6/2011 | Shen et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,148,518 B2 | 4/2012 | Buchanan |
| 8,288,103 B2 | 10/2012 | Oliphant |
| 8,337,851 B2 | 12/2012 | Aukerman |
| 8,343,500 B2 | 1/2013 | Wraith |
| 8,383,338 B2 | 2/2013 | Kitzman |
| 8,460,865 B2 | 6/2013 | Chee |
| 8,481,257 B2 | 7/2013 | Van Eijk |
| 8,481,292 B2 | 7/2013 | Casbon |
| RE44,596 E | 11/2013 | Stroun et al. |
| 8,586,310 B2 | 11/2013 | Mitra |
| 8,614,073 B2 | 12/2013 | Van Eijk |
| 8,685,889 B2 | 4/2014 | Van Eijk |
| 8,741,606 B2 | 6/2014 | Casbon |
| 8,778,849 B2 | 7/2014 | Bowen |
| 8,785,353 B2 | 7/2014 | Van Eijk |
| 8,815,512 B2 | 8/2014 | Van Eijk |
| 8,835,358 B2 | 9/2014 | Fodor |
| 8,865,410 B2 | 10/2014 | Shendure |
| 8,895,249 B2 | 11/2014 | Shen |
| 8,911,945 B2 | 12/2014 | Van Eijk |
| 8,936,912 B2 | 1/2015 | Mitra |
| 8,951,781 B2 | 2/2015 | Reed |
| 9,023,768 B2 | 5/2015 | Van Eijk |
| 9,062,348 B1 | 6/2015 | Van Eijk |
| 9,080,210 B2 | 7/2015 | Van Eijk |
| 9,085,798 B2 | 7/2015 | Chee |
| 9,121,069 B2 | 9/2015 | Lo |
| 9,194,001 B2 | 11/2015 | Brenner |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,340,830 B2 | 5/2016 | Lipson |
| 9,371,598 B2 | 6/2016 | Chee |
| 9,376,716 B2 | 6/2016 | Van Eijk |
| 9,376,719 B2 | 6/2016 | Van Eijk |
| 9,404,156 B2 | 8/2016 | Hicks |
| 9,447,459 B2 | 9/2016 | Van Eijk |
| 9,453,256 B2 | 9/2016 | Van Eijk |

(56) References Cited

U.S. PATENT DOCUMENTS

| | | | |
|---|---|---|---|
| 9,493,820 B2 | 11/2016 | Van Eijk | |
| 9,506,061 B2 | 11/2016 | Brown | |
| 9,574,230 B2 | 2/2017 | Van Eijk | |
| 9,582,877 B2 | 2/2017 | Fu | |
| 9,593,365 B2 | 3/2017 | Frisen et al. | |
| 9,657,335 B2 | 5/2017 | Van Eijk | |
| 9,670,542 B2 | 6/2017 | Van Eijk | |
| 9,702,004 B2 | 7/2017 | Van Eijk | |
| 9,727,810 B2 | 8/2017 | Fodor et al. | |
| 9,745,627 B2 | 8/2017 | Van Eijk | |
| 9,777,324 B2 | 10/2017 | Van Eijk | |
| 9,850,536 B2 | 12/2017 | Oliphant et al. | |
| 9,868,979 B2 | 1/2018 | Chee et al. | |
| 9,896,721 B2 | 2/2018 | Van Eijk | |
| 9,898,576 B2 | 2/2018 | Van Eijk | |
| 9,898,577 B2 | 2/2018 | Van Eijk | |
| 10,023,907 B2 | 7/2018 | Van Eijk | |
| 10,030,261 B2 | 7/2018 | Frisen et al. | |
| 10,095,832 B2 | 10/2018 | Van Eijk | |
| 10,138,509 B2 | 11/2018 | Church et al. | |
| 10,179,932 B2 | 1/2019 | Church et al. | |
| 2002/0040275 A1 | 4/2002 | Cravatt | |
| 2002/0048766 A1 | 4/2002 | Doyle et al. | |
| 2002/0064779 A1 | 5/2002 | Landegren | |
| 2002/0150909 A1 | 10/2002 | Stuelpnagel | |
| 2002/0164611 A1 | 11/2002 | Bamdad | |
| 2002/0168645 A1 | 11/2002 | Taylor | |
| 2003/0040035 A1 | 2/2003 | Slamon | |
| 2003/0064398 A1 | 4/2003 | Barnes | |
| 2003/0087232 A1 | 5/2003 | Christians | |
| 2003/0096323 A1 | 5/2003 | James | |
| 2003/0148335 A1 | 8/2003 | Shen et al. | |
| 2003/0162216 A1 | 8/2003 | Gold | |
| 2003/0170637 A1 | 9/2003 | Pirrung et al. | |
| 2003/0215936 A1 | 11/2003 | Kallioniemi et al. | |
| 2003/0224419 A1 | 12/2003 | Corcoran | |
| 2003/0232382 A1 | 12/2003 | Brennan | |
| 2003/0235852 A1 | 12/2003 | Roberts | |
| 2004/0002090 A1 | 1/2004 | Mayer et al. | |
| 2004/0019005 A1 | 1/2004 | Van Ness | |
| 2004/0023320 A1 | 2/2004 | Steiner et al. | |
| 2004/0067492 A1 | 4/2004 | Peng et al. | |
| 2004/0067493 A1 | 4/2004 | Matsuzaki | |
| 2004/0082059 A1 | 4/2004 | Webb | |
| 2004/0096853 A1 | 5/2004 | Mayer | |
| 2004/0224326 A1 | 11/2004 | Kim et al. | |
| 2004/0259105 A1 | 12/2004 | Fan et al. | |
| 2005/0003431 A1 | 1/2005 | Wucherpfennig | |
| 2005/0019776 A1 | 1/2005 | Callow et al. | |
| 2005/0026188 A1 | 2/2005 | Van Kessel | |
| 2005/0037362 A1 | 2/2005 | Remacle et al. | |
| 2005/0037393 A1 | 2/2005 | Gunderson et al. | |
| 2005/0130188 A1 | 6/2005 | Walt | |
| 2005/0164292 A1 | 7/2005 | Farooqui | |
| 2005/0191656 A1 | 9/2005 | Drmanac et al. | |
| 2005/0196786 A1 | 9/2005 | Levy | |
| 2005/0239192 A1 | 10/2005 | Nasarabadi et al. | |
| 2005/0244850 A1 | 11/2005 | Huang | |
| 2005/0255548 A1 | 11/2005 | Lipovsek et al. | |
| 2005/0260653 A1 | 11/2005 | LaBaer | |
| 2006/0003394 A1 | 1/2006 | Song | |
| 2006/0039823 A1 | 2/2006 | Yamakawa et al. | |
| 2006/0046313 A1 | 3/2006 | Roth | |
| 2006/0079453 A1 | 4/2006 | Sidney et al. | |
| 2006/0134669 A1 | 6/2006 | Casasanta | |
| 2006/0164490 A1 | 7/2006 | Kim et al. | |
| 2006/0188875 A1 | 8/2006 | Cox et al. | |
| 2006/0199207 A1 | 9/2006 | Matysiak | |
| 2006/0211001 A1 | 9/2006 | Yu et al. | |
| 2006/0216775 A1 | 9/2006 | Burkart et al. | |
| 2006/0228758 A1 | 10/2006 | Muchhal et al. | |
| 2006/0263789 A1 | 11/2006 | Kincaid | |
| 2006/0275799 A1 | 12/2006 | Banerjee et al. | |
| 2007/0014810 A1 | 1/2007 | Baker et al. | |
| 2007/0020625 A1 | 1/2007 | Duchaud et al. | |
| 2007/0020640 A1 | 1/2007 | McCloskey et al. | |
| 2007/0020669 A1 | 1/2007 | Ericsson | |
| 2007/0026430 A1 | 2/2007 | Andersen et al. | |
| 2007/0036511 A1 | 2/2007 | Lundquist et al. | |
| 2007/0054288 A1 | 3/2007 | Su et al. | |
| 2007/0099208 A1 | 5/2007 | Drmanac et al. | |
| 2007/0128624 A1 | 6/2007 | Gormley et al. | |
| 2007/0128656 A1 | 6/2007 | Agrawal | |
| 2007/0166725 A1 | 7/2007 | McBride et al. | |
| 2007/0172873 A1 | 7/2007 | Brenner et al. | |
| 2007/0178503 A1 | 8/2007 | Jiang | |
| 2007/0207482 A1 | 9/2007 | Church et al. | |
| 2007/0251824 A1 | 11/2007 | Patton | |
| 2007/0254305 A1 | 11/2007 | Paik et al. | |
| 2007/0269805 A1 | 11/2007 | Hogers | |
| 2007/0280517 A1 | 12/2007 | De La Torre-Bueno et al. | |
| 2008/0009420 A1 | 1/2008 | Schroth et al. | |
| 2008/0032301 A1 | 2/2008 | Rank et al. | |
| 2008/0071071 A1 | 3/2008 | LaBaer et al. | |
| 2008/0108082 A1 | 5/2008 | Rank et al. | |
| 2008/0108804 A1 | 5/2008 | Hayashizaki et al. | |
| 2008/0124252 A1 | 5/2008 | Marchand et al. | |
| 2008/0128627 A1 | 6/2008 | Lundquist et al. | |
| 2008/0153086 A1 | 6/2008 | Wong | |
| 2008/0220434 A1 | 9/2008 | Thomas | |
| 2008/0220981 A1 | 9/2008 | McGregor | |
| 2008/0261204 A1 | 10/2008 | Lexow | |
| 2008/0293591 A1 | 11/2008 | Taussig et al. | |
| 2008/0312103 A1 | 12/2008 | Nemoto et al. | |
| 2009/0006002 A1 | 1/2009 | Honisch et al. | |
| 2009/0018024 A1 | 1/2009 | Church et al. | |
| 2009/0026082 A1 | 1/2009 | Rothberg et al. | |
| 2009/0036323 A1 | 2/2009 | van Eijk et al. | |
| 2009/0082212 A1 | 3/2009 | Williams | |
| 2009/0099041 A1 | 4/2009 | Church et al. | |
| 2009/0105959 A1 | 4/2009 | Braverman et al. | |
| 2009/0117573 A1 | 5/2009 | Fu et al. | |
| 2009/0170713 A1 | 7/2009 | van Eijk et al. | |
| 2009/0192044 A1 | 7/2009 | Fouillet | |
| 2009/0215633 A1 | 8/2009 | van Eijk et al. | |
| 2009/0233802 A1 | 9/2009 | Bignell et al. | |
| 2009/0253581 A1 | 10/2009 | van Eijk et al. | |
| 2009/0280487 A1 | 11/2009 | Hung et al. | |
| 2009/0283407 A1 | 11/2009 | Van Eijk | |
| 2009/0291854 A1 | 11/2009 | Weisinger-Mayr et al. | |
| 2009/0305237 A1 | 12/2009 | Cantor et al. | |
| 2009/0312193 A1 | 12/2009 | Byung-Chul | |
| 2009/0321262 A1 | 12/2009 | Adachi et al. | |
| 2010/0009871 A1* | 1/2010 | Reed | B01J 19/0046 506/26 |
| 2010/0035249 A1 | 2/2010 | Hayashizaki et al. | |
| 2010/0099103 A1 | 4/2010 | Hsieh et al. | |
| 2010/0105052 A1 | 4/2010 | Drmanac et al. | |
| 2010/0111768 A1 | 5/2010 | Banerjee et al. | |
| 2010/0113302 A1 | 5/2010 | Williams | |
| 2010/0120043 A1 | 5/2010 | Sood et al. | |
| 2010/0120098 A1 | 5/2010 | Grunenwald et al. | |
| 2010/0137143 A1 | 6/2010 | Rothberg et al. | |
| 2010/0151464 A1 | 6/2010 | Stuelpnagel et al. | |
| 2010/0159446 A1 | 6/2010 | Haff et al. | |
| 2010/0184614 A1 | 7/2010 | Ye et al. | |
| 2010/0210475 A1 | 8/2010 | Kyu-Sang et al. | |
| 2010/0227329 A1 | 9/2010 | Cuppens | |
| 2010/0282617 A1 | 11/2010 | Rothberg et al. | |
| 2011/0059865 A1 | 3/2011 | Smith et al. | |
| 2011/0152111 A1 | 6/2011 | Illumina | |
| 2011/0244448 A1 | 10/2011 | Shirai et al. | |
| 2011/0245101 A1 | 10/2011 | Chee et al. | |
| 2011/0245111 A1 | 10/2011 | Chee | |
| 2011/0275077 A1 | 11/2011 | James | |
| 2012/0046175 A1 | 2/2012 | Rodesch et al. | |
| 2012/0065081 A1 | 3/2012 | Chee | |
| 2012/0129248 A1 | 5/2012 | Chee et al. | |
| 2012/0135871 A1 | 5/2012 | van Eijk et al. | |
| 2012/0157322 A1* | 6/2012 | Myllykangas | C12Q 1/6853 506/2 |
| 2012/0195810 A1 | 8/2012 | Cohen et al. | |
| 2012/0202698 A1 | 8/2012 | van Eijk et al. | |

(56) References Cited

U.S. PATENT DOCUMENTS

| | | |
|---|---|---|
| 2012/0245053 A1* | 9/2012 | Shirai ............... C12N 15/1093 506/9 |
| 2012/0270748 A1 | 10/2012 | Chee et al. |
| 2013/0096033 A1 | 4/2013 | Routenberg |
| 2013/0261019 A1 | 10/2013 | Lin et al. |
| 2013/0296174 A1 | 11/2013 | Peumans |
| 2014/0079923 A1 | 3/2014 | George et al. |
| 2014/0121118 A1 | 5/2014 | Warner |
| 2014/0155274 A1 | 6/2014 | Xie et al. |
| 2014/0227705 A1 | 8/2014 | Vogelstein et al. |
| 2014/0243224 A1 | 8/2014 | Barnard et al. |
| 2014/0274731 A1 | 9/2014 | Raymond et al. |
| 2014/0296081 A1 | 10/2014 | Diehn et al. |
| 2014/0342921 A1 | 11/2014 | Weiner |
| 2014/0378345 A1 | 12/2014 | Hindson et al. |
| 2015/0005447 A1 | 1/2015 | Berti et al. |
| 2015/0051085 A1 | 2/2015 | Vogelstein et al. |
| 2015/0072867 A1* | 3/2015 | Soldatov ............... B01J 19/0046 506/2 |
| 2015/0087027 A1 | 3/2015 | Makarov et al. |
| 2015/0148239 A1 | 5/2015 | Jon |
| 2016/0003812 A1 | 1/2016 | Porreca et al. |
| 2016/0024576 A1 | 1/2016 | Chee |
| 2016/0289740 A1 | 10/2016 | Fu et al. |
| 2016/0298180 A1 | 10/2016 | Chee |
| 2016/0333403 A1 | 11/2016 | Chee |
| 2017/0058339 A1 | 3/2017 | Chee |
| 2017/0166962 A1 | 6/2017 | van Eijk et al. |
| 2017/0242020 A1 | 8/2017 | Yamauchi et al. |
| 2017/0343545 A1 | 11/2017 | Hadrup et al. |
| 2018/0112209 A1 | 4/2018 | Eshoo |
| 2018/0179591 A1 | 6/2018 | van Eijk |
| 2018/0180601 A1 | 6/2018 | Pedersen et al. |
| 2018/0217094 A1 | 8/2018 | Herr et al. |
| 2018/0247017 A1 | 8/2018 | van Eijk et al. |
| 2018/0291439 A1 | 10/2018 | van Eijk et al. |

FOREIGN PATENT DOCUMENTS

| | | |
|---|---|---|
| EP | 1929039 | 6/2008 |
| EP | 1966393 | 9/2008 |
| EP | 2002017 | 12/2008 |
| EP | 2292788 | 3/2011 |
| EP | 2302070 | 3/2011 |
| EP | 2363504 | 9/2011 |
| EP | 2580351 | 4/2013 |
| EP | 2789696 | 10/2014 |
| EP | 2963127 | 1/2016 |
| EP | 3045544 | 7/2016 |
| EP | 3239304 | 11/2017 |
| JP | 2007-014297 | 1/2007 |
| JP | 2007-074967 | 3/2007 |
| JP | 2009-036694 | 2/2009 |
| JP | 2011-182702 | 9/2011 |
| JP | 2014-217381 | 11/2014 |
| KR | 10-20090081260 | 7/2009 |
| RU | 2145635 | 2/2000 |
| RU | 2270254 | 2/2006 |
| WO | WO 1989/010977 | 11/1989 |
| WO | WO 1991/006678 | 5/1991 |
| WO | WO 1995/025116 | 9/1995 |
| WO | WO 1995/035505 | 12/1995 |
| WO | WO 1998/044151 | 10/1998 |
| WO | WO 1999/032654 | 7/1999 |
| WO | WO 1999/67641 | 12/1999 |
| WO | WO 2000/018957 | 4/2000 |
| WO | WO 2000/024940 | 5/2000 |
| WO | WO 2001/007915 | 2/2001 |
| WO | WO 2001/042796 | 6/2001 |
| WO | WO 2001/090415 | 11/2001 |
| WO | WO 2002/024952 | 3/2002 |
| WO | WO 2002/059355 | 8/2002 |
| WO | WO 2002/059364 | 8/2002 |
| WO | WO 2002/077283 | 10/2002 |
| WO | WO 2002/088396 | 11/2002 |
| WO | WO 2003/002979 | 1/2003 |
| WO | WO 2003/010176 | 2/2003 |
| WO | WO 2004/028955 | 4/2004 |
| WO | WO 2004/067759 | 8/2004 |
| WO | WO 2005/007814 | 1/2005 |
| WO | WO 2005/026387 | 3/2005 |
| WO | WO 2005/042759 | 5/2005 |
| WO | WO 2006/074351 | 7/2006 |
| WO | WO 2006/084130 | 8/2006 |
| WO | WO 2006/117541 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073165 | 6/2007 |
| WO | WO 2007/073171 | 6/2007 |
| WO | WO 2007//073271 | 6/2007 |
| WO | WO 2007/076726 | 7/2007 |
| WO | WO 2007/114693 | 10/2007 |
| WO | WO 2007/120241 | 10/2007 |
| WO | WO 2007/145612 | 12/2007 |
| WO | WO 2007139766 | 12/2007 |
| WO | WO 2008/022332 | 2/2008 |
| WO | WO 2008/069906 | 6/2008 |
| WO | WO 2010/019826 | 2/2009 |
| WO | WO 2009/032167 | 3/2009 |
| WO | WO 2009/036525 | 3/2009 |
| WO | WO 2009/152928 | 12/2009 |
| WO | WO 2009/156725 | 12/2009 |
| WO | WO 2010/019826 | 2/2010 |
| WO | WO 2010/027870 | 3/2010 |
| WO | WO 2010/126614 | 11/2010 |
| WO | WO 2010/127186 | 11/2010 |
| WO | WO 2011/014879 | 2/2011 |
| WO | WO 2011/071943 | 6/2011 |
| WO | WO 2011/127006 | 10/2011 |
| WO | WO 2011/127099 | 10/2011 |
| WO | WO 2011/155833 | 12/2011 |
| WO | WO 2012/022975 | 2/2012 |
| WO | WO 2012/058096 | 5/2012 |
| WO | WO 2012/071428 | 5/2012 |
| WO | WO 2012/139110 | 10/2012 |
| WO | WO 2012/142213 | 10/2012 |
| WO | WO 2012/148477 | 11/2012 |
| WO | WO 2013/123442 | 8/2013 |
| WO | WO 2013/138510 | 9/2013 |
| WO | WO 2013/142389 | 9/2013 |
| WO | 2013150083 A1 | 10/2013 |
| WO | WO 2013/150083 | 10/2013 |
| WO | 2014060483 A1 | 4/2014 |
| WO | WO 2014/142841 | 9/2014 |
| WO | WO 2014/210223 | 12/2014 |
| WO | WO 2014/210225 | 12/2014 |
| WO | WO 2015/085275 | 6/2015 |
| WO | WO 2006/084130 | 8/2016 |
| WO | WO 2016/126882 | 8/2016 |
| WO | WO 2016/138496 | 9/2016 |
| WO | WO 2016/138500 | 9/2016 |
| WO | WO 2016/162309 | 10/2016 |
| WO | WO 2016/168825 | 10/2016 |
| WO | WO 2017019456 | 2/2017 |
| WO | WO 2017/156336 | 9/2017 |
| WO | WO 2018/045181 | 3/2018 |
| WO | WO 2018/045186 | 3/2018 |
| WO | WO 2018/075436 | 4/2018 |
| WO | WO 2018/091676 | 5/2018 |
| WO | WO 2018/144582 | 8/2018 |

OTHER PUBLICATIONS

Angenendt et al., "Cell-free expression and functional assy in a nanowell chip format," Analytical Chemistry, 2004, 76(7):1844-49..
Angenendt et al., "Generation of High Density Protein Microarrays by Cell-free in Situ Expression of Unpurified PCR Products," Molecular and Cellular Proteomics, (2006) Ch. 5.9, pp. 1658-1666.
Bell, "A Simple Way to Treat PCR Products Prior to Sequenceing Using ExoSAP-IT," Biotechniques, 2008, vol. 44, No. 6.

(56) References Cited

OTHER PUBLICATIONS

Blokzul et al., "Profilinq protein expression and interactions: proximity liqation as a tool for personalized medicine," J Intern. Med., 2010, 268:232-245.
Bonfield et al., "The application of numerical estimates of base calling accuracy to DNA sequencing projets," Nucleic Acids Research, 1995, 23(8):1406-1410.
Boulgakov et al., "From Space to Sequece and Bback Again: Iterative DNA Proxiity Ligation and its Applications to DNA-Based Imaging", bioRxiv, 24 pages, 2018.
Brenner et al, "In vitro cloning of coplex mixtures of DNA on microbeads: physical separation of differentially expressed cDNAs," Proc. Natl. Acad. Sci. USA, 2000, 97, 1665-1670.
Carlson et al., "Formylglycine-generating Enzyme," J. of Biological Chemistry, 2008, 283(29):20117-125.
Carter et al., "Stabilaization of an optical microscope to 0.1 nm in three dimensions," Applied Optics, 2007, 46:421-427.
Chatterjee et al., "Protein Microarray On-Demand: A Novel Proteins Microarray System," PLos One, 2008, 3(9):e3265.
Constatine et al., "Use of genechip high-density oligonucleotide arrays for gene expression monitoring," Life Sceiene News, Amersham Life Science; 11-14, 1998.
Carces et al., "An improved ATAC-seq protocol reduces background and enables interrogation of frozen tissues", Nat. Methods. vol. 14(10): pp. 959-962, 2017.
Cujec et al. "Selection of v-abl tyrosine kinase substate sequence from randonmized peptide and cellular proteomic libraries using mRNA display," Chemistry and Biology, 2002, 9:253-264.
Dal et al., "Circle-to-circle amplification for precise and sensitie DNA analysis," Proc. Natl. Acad. Sci., 2004, 101:4548-4553.
Darmants, et al., "ProteinSeq: High-Performance Proteomic Analyses by Proximity, Ligation and Next generation Sequencing," PLos One, 2011, 6(9) e25583.
Dean et al., "Comprehensive human genome amplifiction using multiple displacement amplification," Proc Natl. Acad. Sci. USA 99:5261-66, 2002.
Eagen, "Principles of Chromosomes Architecture Revealed by Hi-C", Trends in Biochemical Sciences, vol. 43, No. 6, 10 pages, 2018.
Ebrwine et al., "Analysis of gene expression in single live neurons," Proc. Natl. Acad. Sci., USA 89, 3010-3014, 1992.
Eberwine, "Ampliication of mRNA Populations Using aRNA Generated from Immobi-lized Oligo(dT)-T7 Primed cDNA," BioTechniques 20 (4), 584, 1996.
Eguiluz et al., "Multitissue array review: A chronological description of tissue array techniques, applications and procedures," Pathology Research and Practice, : 8, 561-568, 2002.
Eldridge et al. "An in itro selection strategy for conferring protease resistance to ligand binding peptides," Protein Eng Des Sel., 22(11): 691-698, 2009.
Eng et al., "Profiling the transcriptone by RNA SPOTS", Nat Methods., 14(12): 1153-1155, 2017.
Forcucci et al., "All-plastic minature fluorescence microscope for point-of-care readout of bead-based bioassays.," J. Biomed Opt. 20 (10): 105010, 15 pages, 2015.
Fredriksson et al., "Multiplexed proximity ligation assays to profile putative plasma biomarkers relevant to pancretic and ovarian cancer," Clin. Chem, 5(3): 582-89, 2008.
Fredruksson et al., "Protein detection using proximity-dependent DNA ligation assays," Nature Biotech., 20: 473-77, 2002.
Frese et al., "Formylglycine Aldehyde Tag-Protein Enginering through a Novel Posttranslational Modification," ChemBioChem., 10: 425-27, 2009.
Gerdtsson et al., "Evaluation of Solid Supports for Slide- and Well-Based Recombinant Antibody Microarrays", Miccroarrays (2016) 5:16, 2016.
Goldkom and Prochop, "A simple and efficient enzymatic mmethod for covalent attachment of DNA to cellulose. Application for hybridization-restriction analysis and for in vitro synthesis of DNA probes.", Nucleic Acids Res. 14: 9171-9191, 1986.

Hedskog et al., "Dynamics of HIV-1 Quasispecies during Antiviral Treatment Dissected usuing Ultra-Deep Pyrosequencing," PLoS One, 5(7): e11345, 2010.
Kap er al., "Histological Assessment of PAXgene Tissue Fixation and Stablization Reagents," PLos One 6, e27704, 10 pages, 2011.
Korlach et al., "Selective aluminum passivation for targeted immobilization of single DNA polymerse in zero-mode waveguide nanostructures," Proc. Natl. Acad. Sci. USA 105, 1176-1181, 2008.
Kurtz et al., "eDNA-Protein Fusions: Covalent Protein-Gene Conjugates for the In Vitro Selection of Peptides and Proteins," ChemBioChem., 2: 666-72, 2001.
Lee et al., "Fluorescent in situ sequencing (FISSEQ) on RNA for gene expression profiling in intact cells and tissues", Nature Protec, 10(3): 442-458, 2015.
Lundberg et al., "High-fidelity amplification using a thermostable DNA polymerase isolated from Pyrococcus furious.," Gene., 108(1): 1-6, 1991.
Lyck, et al., "Immunohistochemical Markers for Quantitative Studies of Neurons and Glia in Human Neocortex," J Histohem Cytochem 56, 201-21, 2008.
MacIntyre, "Unmasking antigens for immunochistochemistry.," Br J Biomed Sci. 58, 190-6, 2001.
Maniatis et al., "Spatiotemporal Dynamic of Molecular Pathology in Amyotrophic Lateral Sclerosis", 54 pages, 2018.
Mir et al., "Sequencing by cyclic ligation and cleavage (CycliC) directly on a microarray captured template," Nucleic Acids Reserch, 37(1): e5-1, 2009.
Mizusawa et al., "A bacteriophage lambda vector for cloning with BamHI and San3A," Gene, 20: 317-322, 1982.
Niemeyer, "The developments of semisynthetic DNA-protein conjugated," Trends-Biotechnol, Sep. 2002, 20(9): 395-401.
Olienikov et al., "Self-assembling protein arrays using electronic semiconductor microchips and in vitro translation," J Proteome Res. May-Jun. 2003, 2(3): 313-319.
Olink Proteomics AB, Proseek® Multiplex 96×96 User Manual, 2016, 12 pages.
Osada et al., "Epitope mapping using ribosome display in a reconstituted cell-free protein synthesis system," j Biochem, May 2009, 145(5): 693-700.
PCT International Preliminary Report on Patentability issued in International Appln. No. PCT/US2010/033064, dated Nov. 1, 2011, 6 pages.
PCT International Preliminary Report on Patentability issued in International Appln. No. PCT/US2010/044134, dated Jan. 31, 2012, 20 pages.
PCT International Preliminary Report on Patentability issued in International Appln. No. PCT/US2010/059327, dated Jun. 12, 2012, 12 pages.
PCT International Preliminary Report on Patentability issued in International Appln. No. PCT/US2011/031163, dated Oct. 9, 2012, 7 pages.
PCT International Preliminary Report on Patentability issued in International Appln. No. PCT/US2011/031308, dated Oct. 9, 2012, 7 pages.
PCT International Preliminary Report on Patentability issued in International Appln. No. PCT/US2012/032759, dated Oct. 8, 2013, 17 pages.
PCT International Search Report and Written Opinion issued in International Appln. No. PCT/EP2013/071645, dated Dec. 11, 2013, 10 pages.
PCT International Search Report and Written Opinion issued in International Appln. No. PCT/US14/29691, dated Aug. 19, 2014, 10 pages.
PCT International Search Report and Written Opinion issued in International Appln. No. PCT/US14/44196, dated Nov. 7, 2014, 15 pages.
PCT International Search Report and Written Opinion issued in International Appln. No. PCT/US14/64588, dated Mar. 11, 2015, 20 pages.
PCT International Search Report and Written Opinion issued in International Appln. No. PCT/US2010/033064, dated Jul. 30, 2010, 8 pages.

(56) References Cited

OTHER PUBLICATIONS

PCT International Search Report and Written Opinion issued in International Appln. No. PCT/US2010/044134, dated Mar. 18, 2011, 16 pages.
PCT International Search Report and Written Opinion issued in International Appln. No. PCT/US2010/059327, dated Mar. 29, 2011, 12 pages.
PCT International Search Report and Written Opinion issued in International Appln. No. PCT/US2011/031163, dated May 23, 2011, 8 pages.
PCT International Search Report and Written Opinion issued in International Appln. No. PCT/US2011/031308, dated Jun. 7, 2011, 8 pages.
PCT International Search Report and Written Opinion issued in International Appln. No. PCT/US2012/032759, dated Sep. 28, 2012, 14 pages.
PCT International Search Report and Written Opinion issued in International Appln. No. PCT/US2014/044191, dated Nov. 7, 2014, 10 pages.
Perler et al., "Intervening sequencing in an Archaea DNA polymerase gene," PNAS USA, Jun. 1992, 89(12): 5577-5581.
Roberts et al., "RNA-peptide fusion for the in vitro selection of peptides and proteins," PNAS USA, Nov. 1997, 94: 12297-122302.
Rouillard et al., "OligoArray 2.0: design o oligonucleotide probes for DNA microarrays usina a thermodynamic approach," Nuc. Acid Research, Jun. 2003. 31(12): 3057-3062.
Rountenberg et al., "Mirofluidic probe: a new tool for integrating microfluidic environments and electronic wafer-orobina," Lab Chip, Oct. 2009, 10: 123-127.
Schlapak et al., "Glass surfaces grafted with high-density poly (ethylene glycol) as substrate for DNA oligonucleotide microarrays," Langimuir, Jan. 2006, 22: 277-285.
Search Report issued in Application No. GB1106254.4, dated Mar. 29, 2012, in 1 page.
Sergeeva et al., "Display technologies: Application for the discovery of drug and gene delivery asents," Advanced Drua Delivery Reviews (2006) 58(15):1622-1654.
Shoemaker et al., "Quantitative phenotypic analysis of yeast deletion mutants using a highly parsllel molecular bar-coding strategy," Nature genetics (1996) 14:450-456.
Spitale et al., "Structural imprints in ivo decode RNA regulatory mechanisms", Nature, 519(7544): 486-90, 2015.
Strell et al., "Placing RNA in context and space-methods for spatially resolves transcriptomics", The FEBS Journal, 14 pages, 2017.
Summersgill et al., "Fluorescence In Situ Hybridization Analysis of Formalim Fixed Paraffin Embedded Tissues, Including Tissue Microarrays," Chapter 4, Bridger, J. Ed., Methods in Molecular Biology 659, 2010, 51-70, 2010.
Takashashi et al., "In Vitro Selection of Protein and Peptide Libraries Using mRNA Display," Nucleic Acid and Peptide Aptamers: Method and Protocols (2009) 535:293-314 (Ch.17).
Thiery et al., "Multiplex target protein imaging in tissue sections by mass spectrometry—TAMSTM," Rapid Commun. Mass Spectrom., 2007, 21:823-829.
Wade et al., "Genome sequence, comparative analysis, and population genetics of the domestic horse,"0 Science., 326: 865-7, 2009.
Wang et al., "Single cell analysis: the new frontier in 'omics'.," Trends Biotechnol., 28: 281-90, 2010.
Weinstein et al., "DNA microscopy: Optic-free spatio-genetic imaging by a stand-alone chemical reaction", bioRxiv, 41 pages. 2018.
Willi-Monnerat et al., "Comprehensie spatiotemporal transcriptomic analyses of the gangliomic eminences demonstrate the uniqueness of its caudal subdivision," Molecular and Cellular Nueorsciences 37: 845-856, 2008.
Wolf et al., "Rapid hybridization kinectics ofDNA attached to submicron latex particles", Nucleic Acids Res 15: 2911-2926, 1987.
Worthington et al., "Clonng of random oligonucleotides to create single-insert plasmid libraries," Analyt. Biochem, 2001, 294:169-175.
Zhang et al., "Assembling DNA through Affinity Binding to Achieve Ultrasensitive Protein Detection," Ansew Chem Int Ed (2013) 52:2-10.
Zlobec et al., "Next-generation tissue microarray (ngTMA) increase the quality of biomarker studies: an example using CD3, CD8, and CD45RO in the tumor microenviroment of six different solid tumor t es," Journal of Translational Medicine 2013 11:104.
Crosetto: "Spatially resolved transcriptomics and beyond", Nature Review Genetics, Jan. 1, 2015 (Jan. 1, 2015), pp. 57-66, XP055284555, Retrieved from the Internet: URL:http://www.nature.com/nrg/joumal/vl6/nl/pdf/nrg3832.pdf [retrieved on Jun. 29, 2016].
International Search Report and Written Opinion dated Aug. 5, 2016 in PCT/EP2016/057355.
U.S. Appl. No. 61/839,313, dated Jun. 25, 2013, Chee et al.
U.S. Appl. No. 61/839,320, dated Jun. 25, 2013, Chee et al.
U.S. Appl. No. 61/902,105, dated Nov. 8, 2013, Kozlov et al.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003.
Affymetrix, "Human Genome U95Av2," Internet Citation, retrieved from the internet: on the World Wide Web affymetrix.com, retrieved on Oct. 2, 2002.
Albretsen et al., "Applications of magnetic beads with covalently attached oligonucleotides in hybridization: Isolation and detection of specific measles virus mRNA from a crude cell lysate", Anal. Biochem. 189: 40-50, 1990.
Allawi and SantaLucia, "Thermodynamics and NMR of Internal GâT Mismatches in DNA," Biochemistry, 36:10581-94.
Anderson et al., "Microarrayed Compound Screening to Identify Activators and Inhibitors of AMP-Activated Protein Kinase," J. of Biomolecular Screening, 2004, 9:112.
Andersson et al., "Analysis of protein expression in cell microarrays: a tool for antibody-based proteomics.," J Histochem Cytochem., 4(12): 1413-1423, 2006.
Andresen et al., "Deciphering the Antibodyome—Peptide Arrays for Serum Antibody Biomarker Diagnostics," Current Proteomics, 6(1), 1-12, 2009.
Angenendt et al., "Cell-free Protein expression and functional assay in a nanowell chip format," Analytical Chemistry, 2004, 76(7):1844-49.
Angenendt et al.,"Generation of High Density Protein Microarrays by Cell-free in Situ Expression of Unpurified PCR Products," Molecular and Cellular Proteomics, (2006) Ch. 5.9, pp. 1658-66.
Armani et al, "2D-PCR: a method of mapping DNA in tissue sections," Lab on a Chip, 2009, 9(24):3526-34.
Asp et al., "Spatial detection of fetal marker genes expressed at low level in adult human heart tissue", Scientific Reports, 7: 12941, 10 pages, 2017.
Atkinson and Wells, "An Updated Protocol for High Throughput Plant Tissue Sectioning.", Front Plant Sci, 8: 1721, 2017.
Atkinson, Overview of Translation: Lecture Manuscript, U of Texas (2000) DD. 6.1-6.8.
Bains et al, "A Novel Method for Nucleic Acid Sequence Determination", Journal of Theoretical Biology, 1988, 135(3), 303-7.
Baird et al., "Rapid SNP Discovery and Genetic Mapping Using Sequenced RAD markers," PLOS One, 2008, 3(1 0):e3376.
Barnes, "PCR amplification of up to 35-kb DNA with high fidelity and high yield from lambda bacteriophage templates.," Proc. Natl. Acad. Sci USA, 91: 2216-2220, 1994.
Baugh et al, "Quantitative analysis of mRNA amplification by in vitro transcription," Nucleic Acids Res., 2001, 29:5:e29.
Bell, "A Simple Way to Treat PCR Products Prior to Sequencing Using ExoSAP-IT," . Biotechniques, 2008, vol. 44, No. 6.
Bentley et al, "Accurate whole human genome sequencing using reversible terminator chemistry", Nature, 2008, 456:53-59.
Bielas et al., "Human cancers express a mutator phenotype," Proc. Natl. Acad. Sci. USA, 2006, 103(48): 18238-18242.
Bielas et al., "Quantification of random genomic mutations," Nat. Methods, 2005, 2(4):285-290.
Birney, et al, "Identification and analysis of functional elements in 1% of the human genome by the ENCODE pilot project," Nature, 2007, 447:799-816.

(56) References Cited

OTHER PUBLICATIONS

Blokzijl et al., "Profiling protein expression and interactions: proximity ligation as a tool for personalized medicine," J Intern. Med., 2010, 268:232-245.
Blow, "Tissue Issues," Nature, 448(23), 959-962, 2007.
Bonfield et al., "The application of numerical estimates of base calling accuracy to DNA sequencing projects," Nucleic Acids Research, 1995, 23(8):1406-1410.
Boulgakov et al., "From Space to Sequence and Back Again: Iterative DNA Proximity Ligation and its Applications to DNA-Based Imaging", bioRxiv, 24 pages, 2018.
Bowtell, "The genesis and evolution of high-grade serous ovarian cancer," Nat. Rev. Cancer, 2010, (11 ):803-808 Abstract.
Brandon et al., "Mitochondrial mutations in cancer," Oncogene, 2006, 25(34):4647-4662.
Brenner et al, "In vitro cloning of complex mixtures of DNA on microbeads: physical separation of differentially expressed cDNAs," Proc. Natl. Acad. Sci. USA, 2000, 97, 1665-1670.
Brenner et al., "Gene expression analysis by massively parallel signature sequencing (MPSS) on microbead arrays", Nat. Biotech. 18: 630-634, 2000.
Brockman et al., "Quality scores and SNP detection in sequencing-by-synthesis systems," Methods, 2008, 18:763-770.
Burgess, "A space for transcriptomics", Nature Reviews Genetics | Published online Jul. 15, 2016; doi:10.1038/nrg.2016.94.
Burgess, "Finding structure in gene expression", Nature Reviews Genetics | Published online Apr. 13, 2018; doi:10.1038/nrg.2018.19.
Burns et al., "Well-less, gel-permeation formats for ultra-HTS," DDT, 2001, 6(12):S40-S47.
Burton et al., "Coverslip Mounted-Immersion Cycled in Situ RT-PCR for the Localization of mRNA in Tissue Sections," Biotechniques, 1998, 24; pp. 92-100.
Carlson et al., "Function and Structure of a Prokaryotic Formylglycine-generating Enzyme," J. of Biological Chemistry, 2008, 283(29):20117-125.
Carter et al., "Stabilization of an optical microscope to 0.1 nm in three dimensions," Applied Optics, 2007, 46:421-427.
Cerutti et al., "Generation of sequence-specific, high affinity anti-DNA antibodies," Journal of Biological Chemistry, 2001, 276(16):12769-12773.
Cha et al., "Specificity, Efficiency and Fidelity of PCR," Genome Res., 1993, 3:518-29.
Chandra et al., "Cell-free synthesis-based protein microarrays and their applications," Proteomics, 2009, 5(6):717-30.
Chatterjee et al., "Protein Microarray On-Demand: A Novel Protein Microarray System," PLos One, 2008, 3(9):e3265
Chatterjee, et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23:1878-1882.
Chen et al., "Expansion Microscopy," 2015, Science. 347(6221):543-548.
Chen et al., "Spatially resolved, highly multiplexed RNA profiling in single cells", Science 348(6233), 36 pages, 2015.
Cheng et al., "Sensitive Detection of Small Molecules by Competitive Immunomagnetic-Proximity Ligation Assay," Anal Chem, 2012, 84:2129-2132.
Condina et al., "A sensitive magnetic bead method for the detection and identification of tyrosine phosphorylation in proteins by MALDI-TOF/TOF MS," Proteomics, 2009, 9:3047-3057.
Constantine et al.,"Use of genechip high-density oligonucleotide arrays for gene expression monitoring," Life Sceience News, Amersham Life Science; 11-14, 1998.
Copeland et al., "Mitochondrial DNA Alterations in Cancer," Cancer Invest., 2002, 557-569.
Corces et al., "An improved ATAC-seq protocol reduces background and enables interrogation of frozen tissues", Nat. Methods. vol. 14(10): pp. 959-962, 2017.
Cujec et al. "Selection of v-abl tyrosine kinase substate sequences from randomnized peptide and cellular proteomic libraries using mRNA display," Chemistry and Biology, 2002, 9:253-264.
Dahl et al., "Circle-to-circle amplification for precise and sensitive DNA analysis," Proc. Natl. Acad. Sci., 2004, 101:4548-4553.
Darmanis, et al.,"ProteinSeq: High-Performance Proteomic Analyses by Proximity, Ligation and Next Generation Sequencing," PLos One, 2011, 6(9):e25583.
Daubendiek et al., "Rolling-Circle RNA Synthesis: Circular Oligonucleotides as Efficient Substrates for T7 RNA Polymerase," J. Am. Chem. Soc., 1995, 117:77818-7819.
Davies et al., "How best to identify chromosomal interactions: a comparison of approaches.", Nat. Methods 14, 125-134, 2017.
Dean et al., "Comprehensive human genome amplification using multiple displacement amplification," Proc Natl. Acad. Sci. USA 99:5261-66, 2002.
Dhindsa et al., "Virtual Electrowetting Channels: Electronic Liquid Transport with Continuous Channel Functionality," Lab Chip, 2010, 10:832-836.
Dressman et al., "Transforming single DNA molecules into fluorescent magnetic particles for detection and enumeration of genetic variations," Proc. Natl. Acad. Sci. USA, 2003, 100:8817-8822.
Drmanac et al., "Accurate sequencing by hybridization for DNA diagnostics and individual genomics," Nature Biotechnology, 16:54-58, 1998.
Druley et al., "Quantification of rare allelic variants from pooled genomic DNA," Nat. Methods 6: 263-65, 2009.
Duncan et al., "Affinity chromatography of a sequence-specific DNA binding protein using teflon-linked oligonucleotides", Anal. Biochem. 169: 104-108, 1988.
Eagen, "Principles of Chromosome Architecture Revealed by Hi-C", Trends in Biochemical Sciences, vol. 43, No. 6, 10 pages, 2018.
Eberwine et al., "Analysis of gene expression in single live neurons," Proc. Natl. Acad. Sci., USA 89, 3010-3014, 1992.
Eberwine, "Amplification of mRNA Populations Using aRNA Generated from Immobi-lized Oligo(dT)-T7 Primed cDNA," BioTechniques 20 (4), 584, 1996.
Eguiluz et al., "Multitissue array review: A chronological description of tissue array techniques, applications and procedures," Pathology Research and Practice, 2006, 202:561-568.
Eldridge et al. "An in vitro selection strategy for conferring protease resistance to ligand binding peptides," Protein Eng Des Sel., 22(11): 691-698, 2009.
Ellington et al., "Antibody-based protein multiplex platforms: technical and operational challenges," Clin Chem 56(2): 186-193, 2010.
Eng et al., "Profiling the transcriptome by RNA SPOTs", Nat Methods., 14(12): 1153-1155, 2017.
Extended European Search Report issued in European Appln. No. 19159432.4, dated Jul. 19, 2019, 6 pages.
Fan et al., " Highly parallel SNP genotyping," Cold Spring Symp. Quant. Biol., 68: 69-78, 2003.
Fire and Xu, "Rolling replication of short DNA circles," Proc. Natl. Acad. Sci., 92: 4641-4645, 1995.
Flanigon et al., "Multiplex protein detection with DNA readout via mass spectrometry," N. Biotechnol., 30(2): 153-158, 2013.
Fodor et al., "Light-Directed, Spatially Addressable Parallel Chemical Synthesis," Science, 251(4995), 767-773, 1995.
Forcucci et al., "All-plastic miniature fluorescence microscope for point-of-care readout of bead-based bioassays.," J. Biomed Opt. 20 (10): 105010, 15 pages, 2015.
Fredriksson et al., "Multiplexed protein detection by proximity ligation for cancer detection," Nature Methods, 4(4): 327-29, 2007.
Fredriksson et al., "Multiplexed proximity ligation assays to profile putative plasma biomarkers relevant to pancreatic and ovarian cancer," Clin. Chem., 5(3): 582-89, 2008.
Fredriksson et al., "Protein detection using proximity-dependent DNA ligation assays," Nature Biotech., 20: 473-77, 2002.
Frese et al., "Formylglycine Aldehyde Tag-Protein Engineering through a Novel Posttranslational Modification," ChemBioChem., 10: 425-27, 2009.
Fu et al., "Counting individual DNA molecules by the stochastic attachment of diverse labels," PNAS, 108: 9026-9031, 2011.

(56) References Cited

OTHER PUBLICATIONS

Fullwood et al., "Next-generation DNA sequencing of paired-end tags (PET) for transcriptome and genome analyses," Genome Res., 19: 521-532, 2009.
Gao et al., "High density peptide microarrays. In situ synthesis and applications," Molecular Diversity, 8, 177-187, 2004.
Gao et al., "Q&A: Expansion microscopy", BMC Biology, 15: 50, 9 pages, 2017.
Gerdtsson et al., "Evaluation of Solid Supports for Slide- and Well-Based Recombinant Antibody Microarrays", Microarrays (2016) 5:16, 2016.
Giacomello et al., "Spatially resolved transcriptome profiling in model plant species", Nature Plants 3, 17061, 11 pages, 2017.
Gnanapragasam, "Unlocking the molecular archive: the emerging use of formalin-fixed paraffin-embedded tissue for biomarker research in urological cancer," BJU International,105, 274-278, 2009.
Goldkom and Prockop, "A simple and efficient enzymatic method for covalent attachment of DNA to cellulose. Application for hybridization-restriction analysis and for in vitro synthesis of DNA probes.", Nucleic Acids Res. 14: 9171-9191, 1986.
Gu et al., "Protein tag-mediated conjugation of oligonucleotides to recombinant affinity binders for proximity ligation," N Biotechnol., 30(2): 144-152, 2013.
Gunderson et al., "Decoding Randomly Ordered DNA Arrays," Genome Research 14: 870-877, 2004.
Hammond et al., "Profiling cellular protein complexes by proximity ligation with dual tag microarray readout," 7(7): e40405, 2012.
Han et al., "3C and 3C-based techniques: the powerful tools for spatial genome organization deciphering", Molecular Cytogenetics (2018) 11: 21, 10 pages, 2018.
He et al., "In situ synthesis of protein arrays," Current Opinion in Biotechnology, 19: 4-9, 2008.
He et al., "Printing protein arrays from DNA arrays," Nature Methods, 5: 175-77, 2008.
He, "Cell-free protein synthesis: applications in proteomics and biotechnology," New Biotechnology 25: 126-132, 2008.
Hedskog et al., "Dynamics of HIV-1 Quasispecies during Antiviral Treatment Dissected using Ultra-Deep Pyrosequencinq," PLoS One, 5(7): e11345, 2010.
Hejatko et al., "In Situ Hybridization Techniques for mRNA Detection in Whole Mount *Arabidopsis* Samples," Nature Protocols, 2006, 1(4):1939-1946.
Hein et al., "Click Chemistry, A Powerful Tool for Pharmaceutical Sciences", Pharm Res., 25(10): 2216-2230, 2008.
Hiatt et al., "Parallel, tag-directed assembly of locally-derived short sequence reads," Nature Methods, 7(2): 119-25, 2010.
Inoue and Wittbrodt, "One for All—A Highly Efficient and Versatile Method for Fluorescent Immunostaining in Fish Embryos," PLoS One 6, e19713, 2011.
Jabara et al., Accurate sampling and deep sequencing of the HIV-1 protease gene using a Primer ID. PNAS 108(50); 20166-20171, 2011.
Jamur and Oliver, "Permeabilization of cell membranes.," Method Mal. Biol., 588: 63-66, 2010.
Jemt et al., "An automated approach to prepare tissue-derived spatially barcoded RNA-sequencing libraries", Scientific Reports, 6: 37137, 10 pages, 2016.
Jones et al., Comparative lesion sequencing provides insights into tumor evolution. Proc. Natl. Acad. Sci. USA 105(11): 4283-4288, 2008.
Kanehisa, "Use of statistical criteria for screening potential homologies in nucleic acid sequences ", Nucleic Acids Res. 12: 203-213, 1984.
Kap et al., "Histological Assessment of PAXgene Tissue Fixation and Stabilization Reagents," PLoS One 6, e27704, 10 pages, 2011.
Kolb et al., "Click Chemistry: Diverse Chemical Function from a Few Good Reactions.", Angew. Chem. Int. Ed., 40(11): 2004-2021, 2001.

Kolovos et al., "Investigation of the spatial structure and interactions of the genome at sub-kilobasepair resolution using T2C.", Nat. Protoc. 13, 459-477, 2018.
Korbel et al., "Paired-End Mapping Reveals Extensive Structural Variation in the Human Genome," Science, 318(5849): 420-426, 2007.
Korlach et al., "Selective aluminum passivation for targeted immobilization of single DNA polymerase molecules in zero-mode waveguide nanostructures," Proc. Natl. Acad. Sci. USA 105, 1176-1181, 2008.
Kozlov et al., "A High-Complexity Multiplexed Solution-Phase Assay for Profiling Protease Activity on Microarrays," Comb. Chem. and Hiah Throuahout, 11: 24-35, 2008.
Kozlov et al., "A Highly Scalable Peptide-Based Assay System for Proteomics," PLoS ONE, 7(6): e37441, 2012.
Kozlov et al., "A Method for Rapid Protease Substrate Evaluation and Optimization," Comb. Chem. and Hiah Throuahout, 9: 481-87, 2006.
Kurz et al., "eDNA-Protein Fusions: Covalent Protein-Gene Conjugates for the in Vitro Selection of Peptides and Proteins," ChemBioChem., 2: 666-72, 2001.
Lage et al., "Whole Genome Analysis of Genetic Alterations in Small DNA Samples Using Hyperbranched Strand Displacement Amplification and Array—CGH," Genome Research 13: 294-307, 2003.
Langdale et al., "A rapid method of gene detection using DNA bound to Sephacryl", Gene 36: 201-210, 1985.
Larman et al., "Autoantigen discovery with a synthetic human peptidome," Nature Biotechnology, doi:1 0.1038/nbt.1856, vol. 29, No. 6, pp. 535-541, 2011.
Lassmann et al., A Novel Approach for Reliable Microarray Analysis of Microdissected Tumor Cells From Formalin-Fixed and Paraffin-Embedded Colorectal Cancer Resection Specimens, J Mol Med, 87, 211-224, 2009.
Lee et al., "Fluorescent in situ sequencing (FISSEQ) of RNA for gene expression profiling in intact cells and tissues", Nature Protec, 10(3): 442-458, 2015.
Lee et al., "Highly multiplexed subcellular RNA sequencing in situ", Science, 343(6177): 1360-1363, 2014.
Lein et al., "The promise of spatial transcriptomics for neuroscience in the era of molecular cell typing", Science 358, 64-69, 2017.
Leriche et al., "Cleavable linkers in chemical biology.", Bioorganic & Medicinal Chemistry, 20: 571-582, 2012.
Levene et al., "Zero-Mode Waveguides for Single-Molecule Analysis at High Concentrations," Science 299, 682-686, 2003.
Li et al., "A photocleavable fluorescent nucleotide for DNA sequencing and analysis," Proc. Natl. Acad. Sci., 100: 414-419, 2003.
Linnarsson, "Recent advances in DNA sequencing methods—general principles of sample preparation," Experimental Cell Research, 316: 1339-1343, 2010.
Lizardi et al., "Mutation detection and single-molecule counting using isothermal rolling-circle amplification," Nat. Genet. 19: 225-232, 1998.
Lovatt et al., "Transcriptome in vivo analysis (TIVA) of spatially defined single cells in live tissue.", Nature Methods 11, 190-196, 2014.
Lund et al., "Assessment of methods for covalent binding of nucleic acids to magnetic beads, Dynabeads, and the characteristics of the bound nucleic acids in hybridization reactions.", Nucleic Acids Res., 16: 10861-80, 1988.
Lundberg et al., "High-fidelity amplification using a thermostable DNA polymerase isolated from *Pyrococcus furiosus*.," Gene., 108(1): 1-6, 1991.
Lundberg et al., "Homogeneous antibody-based proximity extension assays provide sensitive and specific detection of low-abundant proteins in human blood," Nucleic Acids Res., 39(15): e102, 2011.
Lundberg et al., "Multiplexed homogeneous proximity ligation assays for high-throughput protein biomarker research in serological material," Mol Cell Proteomics, 10(4): M110.004978, 2011.
Lundquist et al., "Parallel confocal detection of single molecules in real time," Opt. Lett. 33, 1026-1028, 2008.

(56) References Cited

OTHER PUBLICATIONS

Lyck, et al., "Immunohistochemical Markers for Quantitative Studies of Neurons and Glia in Human Neocortex," J Histochem Cytochem 56, 201-21, 2008.
MacIntyre, "Unmasking antigens for immunohistochemistry.," Br J Biomed Sci. 58, 190-6, 2001.
Macosko et al., "Highly Parallel Genome-wide Expression Profiling of Individual Cells Using Nanoliter Droplets," Cell 161, 1202-1214, 2015.
Maniatis et al., "Spatiotemporal Dynamics of Molecular Pathology in Amyotrophic Lateral Sclerosis", 54 pages, 2018.
McCloskey et al., "Encoding PCR Products with Batch-stamps and Barcodes.," Biochem. Genet. 45: 761-767, 2007.
Mcgee, "Structure and Analysis of Affymetrix Arrays," UTSW Microarray Analysis Course, Oct. 28, 2005.
McKernan et al., "Sequence and structural variation in a human genome uncovered by short-read, massively parallel ligation sequencing using two-base encoding," Genome Res., 19: 1527-41, 2009.
Metzker "Sequencing technologies—the next generation," Nature Reviews Genetics, 11: 31-46, 2010.
Miller et al., "Basic Concepts of Microarrays and Potential Applications in Clinical Microbiology," Clinical Microbiology Reviews, vol. 22, No. 4, pp. 611-633, 2009.
Mir et al., "Sequencing by cyclic ligation and cleavage (CycliC) directly on a microarray captured template," Nucleic Acids Research, 37(1): e5-1, 2009.
Mishra and Hawkins, Three-dimensional genome architecture and emerging technologies: looping in disease. Genome Med. 9, 87, 14 pages, 2017.
Mishra, "Three-dimensional genome architecture and emerging technologies: looping in disease", Genome Medicine, 9: 87, 14 pages, 2017.
Mitsuhashi et al., "Gene manipulation on plastic plates," Nature 357: 519-520, 1992.
Mizusawa et al., "A bacteriophage lambda vector for cloning with BamHI and Sau3 A," Gene, 20: 317-322, 1982.
Moncada et al., "Building a tumor atlas: integrating single-cell RNA-Seq data with spatial transcriptomics in pancreatic ductal adenocarcinoma", Institute for Computational Medicine, bioRxiv, 28 pages, 2018.
Moor et al., "Spatial transcriptomics: paving the way for tissue-level systems biology", Science Direct, Current Opinion in Biotechnology, 46: 126-133, 2017.
Mortazavi et al., "Mapping and quantifying mammalian transcriptomes by RNA-Seq," Nature Methods, 5(7): 621-8, 2008.
Nawy, "Spatial transcriptomics", Nature Methods, vol. 15, No. 1, 2018.
Ng et al., "Gene identification signature (GIS) analysis for transcriptome characterization and genome annotation," Nature Methods, 2(2): 105-111, 2005.
Ng et al., "Massively parallel sequencing and rare disease," Human Malec. Genetics, 19(2): R119-R124, 2010.
Ng et al., "Multiplex sequencing of paired-end ditags (MS-PET): a strategy for the ultra-high-throughput analysis of transcriptomes and genomes," Nucleic Acids Research, Jul. 2006, 34(12): e84, 10 pages.
Niemeyer, "The developments of semisynthetic DNA-protein conjugates," TrendsBiotechnol, Sep. 2002, 20(9): 395-401.
Nuovo, "In situ PCR: protocols and applications.," Genome Res, Feb. 1995, 4 (4):151-167.
Oleinikov et al., "Self-assembling protein arrays using electronic semiconductor microchips and in vitro translation," J Proteome Res, May-Jun. 2003, 2(3): 313-319.
Olink Proteomics AB, Proseek® Multiplex 96x33 96 User Manual, 2016, 12 pages.
Osada et al., "Epitope mapping using ribosome display in a resconstituted cell-free protein synthesis system," J Biochem, May 2009, 145(5): 693-700.
O-Shannessy et al., "Detection and quantitation of hexa-histidine-tagged recombinant proteins on western blots and by a surface plasmon resonance biosensor technique," Anal Biochem, 229(1): 119-124, 1995.
PCT International Search Report and Written Opinion issued in International Appln. No. PCT/EP2016/057355, dated Aug. 5, 2016, 8 pages.
Perler et al., "Intervening sequences in an Archaea DNA polymerase gene," PNAS USA, Jun. 1992, 89(12): 5577-5581.
Petterson et al., "Generations of sequencing technologies," Genomics, 2009, 105-111.
Polsky-Cynkin et al., "Use of DNA Immobilizedon Plastic and Agarose Supports to DetectDNA by SandwichHybridization", Clin. Chem. 31: 1438-1443, 1985.
Rajeswari et al., "Multiple pathogen biomarker detection using an encoded bead array in droplet PCR," J. Microbial Methods, Aug. 2017, 139:22-28.
Ramachandran et al., "Next-generation high-density self-assembling functional protein arrays," Nature Methods, Jun. 2008, 5(6):535-538.
Ranki et al., "Sandwich hybridization as a convenient method for the detection of nucleic acids in crude samples", Gene 21: 77-85, cellulose, 1983.
Roberts et al., "RNA-peptide fusions for the in vitro selection of peptides and proteins," PNAS USA, Nov. 1997, 94: 12297-122302.
Ronaghi et al., "A sequencing method based on real-time pyrophosphate," Science, Jul. 1998, 281(5375): 363-365.
Ronaghi et al., "Real-time DNA sequencing using detection of pyrophosphate release," Analytical Biochemistry, Nov. 1996, 242(1): 84-89.
Ronaghi, "Pyrosequencing sheds light on DNA sequencing," Genome Res, Jan. 2001, 11(1):3-11.
Rouillard et al., "OligoArray 2.0: design of oligonucleotide probes for DNA microarrays using a thermodynamic approach," Nuc. Acid Research, Jun. 2003, 31(12): 3057-3062.
Rountenberg et al., "Microfluidic probe: a new tool for integrating microfluidic environments and electronic wafer-orobina," Lab Chip, Oct. 2009, 10: 123-127.
Rubin et al., "Whole-genome resequencing reveals loci under selection during chicken domestication.," Nature, Mar. 2010, 464: 587-591.
Rush et al., "New Aldehyde Tag Sequences Identified by Screening Formylglycine Generating Enzymes in Vitro and in Vivo," J. of American Chemical Society, Aug. 2008, 130(37): 12240-12241.
Rusk, "Spatial transcriptomics", Nature Methods, vol. 13, No. 9, 2016.
Salem et al., "Multidimensional transcriptomics provides detailed information about immune cell distribution and identity in HER2+ breast tumors", bioRxiv, 41 pages, 2018.
Schaus et al., "A DNA nanoscope via auto-cycling proximity recording.", Nat. Commun. 8, 696, 10 pages, 2017.
Schena et al., "Quantitative monitoring of gene expression patterns with a complementary DNA microarray," Science, Oct. 1995, 270(5235): 467-470.
Schena et al., "Entering the Postgenome Era," Science, 1995, 270:368-9, 371.
Schlapak et al., "Glass surfaces grafted with high-density poly (ethylene glycol) as substrates for DNA oligonucleotide microarrays," Langinuir, Jan. 2006, 22: 277-285.
Schmitt et al., "Detection of ultra-rare mutations by next-generation sequencing," PNAS (2012) 109:14508-14523.
Sergeeva et al., "Display technologies: Application for the discovery of drug and gene delivery aaents," Advanced Drua Delivery Reviews (2006) 58(15):1622-1654.
Seurynck-Servoss et al., "Evaluation of Surface Chemistries for Antibody Microarrays", Anal Biochem., 371(1): 105-115, 2007.
Shelbourne et al., "Fast copper-free click DNA ligation by the ring-strain promoted alkyne-azide cycloaddition reaction.", Chem. Commun., 47: 6257-6259, 2011.
Shendure et al., "Accurate Multiplex Polony Sequencing of an Evolved Bacterial Genome," Science, 2005, 309:1728-1732.

(56) References Cited

OTHER PUBLICATIONS

Shi et al., "The MicroArray Quality Control (MAQC) project shows inter- and intraplatform reproducibility of gene expression measurements," Nature Biotechnology, 2006, 24(9):1151-61.
Shirai et al., "Novel Tools for Analyzing Gene Expressions in Single Cells," the 5th International Workshop on Approaches to Single-Cell Analysis, The University of Tokyo, Mar. 3-4, 2011, 1 page.
Shoemaker et al., "Quantitative phenotypic analysis of yeast deletion mutants using a highly parallel molecular bar-coding strategy," Nature genetics (1996) 14:450-456.
Shults et al., "A multiplexed protein kinase assay," Chem Bio Chem (2007) 8:933-942.
Sievertzon et al., "Transcriptome analysis in primary neural stem cells using a tag cDNA amplification method," BMC Neuroscience, Dec. 2005, 6: 28.
Slonim and Yanai, "Getting started in gene expression microarray analysis," Plos Computational Biology, 2009, 5(10):e1000543.
Soni and Meller, "Progress toward ultrafast DNA sequencing using solid-state nanopores," Clin Chem., 2007, 53: 1996-2001.
Spitale et al., "Structural imprints in vivo decode RNA regulatory mechanisms", Nature, 519(7544): 486-90, 2015.
Spurgeon et al., "High Throughput Gene Expression Measurement with Real Time PCR in a Microfluidic Dynamic Array," PlosONE, 2008, 3(2):e1662.
Stahl et al., "Visualization and analysis of gene expression in tissue sections by spatial transcriptomics.", Science 353, 78-82, 2016.
Strell et al., "Placing RNA in context and space—methods for spatially resolved transcriptomics", The FEBS Journal, 14 pages, 2017.
Summersgill et al., "Fluorescence In Situ Hybridization Analysis of Formalin Fixed Paraffin Embedded Tissues, Including Tissue Microarrays," Chapter 4, Bridger, J. Ed., Methods in Molecular Biology 659, 2010, 51-70, 2010.
Sun et al., "Direct immobilization of DNA probes on non-modified plastics by UV irradiation and integration in microfluidic devices for rapid bioassay," Anal. Bio. Chem., 402: 741-748, 2012.
Takahashi et al., "In Vitro Selection of Protein and Peptide Libraries Using mRNA Display," Nucleic Acid and Peptide Aptamers: Methods and Protocols (2009) 535:293-314 (Ch.17).
Tang et al., "RNA-Seq analysis to capture the transcriptome landscape of a single cell.," Nat Protoc., 5: 516-35, 2010.
Taniguchi et al., "Quantitative analysis of gene expression in a single cell by qPCR," Nature Methods, 6, pp. 503-506, 2009.
Taylor et al., "Mitochondrial DNA mutations in human disease." Nature Reviews Genetics. May 2005, 6(5):389-402.
Tentori et al., "Detection of Isoforms Differing by a Single Charge Unit in Individual Cells.", Chem. Int. Ed., 55, 12431, 2016.
Thiery et al., "Multiplex target protein imaging in tissue sections by mass spectrometry—TAMSIM," Rapid Commun. Mass Spectrom., 2007, 21:823-829.
Thornton, "High rate thick film growth." Annual review of materials science, Aug. 1977, 7(1):239-60.
Tian et al., "Antigen peptide-based immunosensors for rapid detection of antibodies and antigens," Anal Chem May 26, 2009, 81 (13):5218-5225.
Tijssen, "Overview of principles of hybridization and the strategy of nucleic acid assays" in Techniques in 5 Biochemistry and Molecular Biology—Hybridization with Nucleic Acid Probes 1993.
Tolbert et al., "New Methods for Proteomic Research: Preparation of Proteins with N-Terminal Cysteines for Labeling and Conjugation" Angewandte Chemie International Edition, Jun. 17, 2002, 41(12):2171-4.
Valencia et al., "mRNA-Display-Based Selections for Proteins with Desired Functions: A Protease-Substrate Case Study." Biotechnology progress, May 2008, 24(3):561-9.
Van Gelder et al., "Amplified RNA synthesized from limited quantities of heterogeneous cDNA," Proc. Natl. Acad. Sci. USA 87, 1663-1667, 1990.

Van Ness et al., "A versatile solid support system for oligodeoxynucleotide probe-based hybridization assays", Nucleic Acids Res. 19: 3345-3350, 1991.
Velculescu et al., "Serial analysis of gene expression." Science, Oct. 20, 1995, 270(5235):484-7.
Vickovic et al., "Massive and parallel expression profiling using microarrayed single-cell sequencing," Nature Communications, Oct. 14, 2016; 7:13182. doi: 10.1038/ncomms13182.
Vogelstein et al., "Digital PCR," Proceedings of the National Academy of Sciences, Aug. 3, 1999, 96:9236-9241.
Wade et al., "Genome sequence, comparative analysis, and population genetics of the domestic horse.," Science., 326: 865-7, 2009.
Waichman et al., "Functional immobilization and patterning of proteins by an enzymatic transfer reaction." Analytical chemistry, Jan. 21, 2010, 82(4):1478-85.
Walker et al., "Strand displacement amplification—an isothermal, in vitro DNA amplification technique." Nucleic acids research. Apr. 11, 1992, 1992 20(7):1691-1696.
Wang et al., "Single cell analysis: the new frontier in 'omicsi'.,"Trends Biotechnol., 28: 281-90, 2010.
Wang et al., "Three-dimensional intact-tissue sequencing of single-cell transcriptional states", Science, 361(6400), 22 pages, 2018.
Wang et al., "High-fidelity mRNA amplification for gene profiling." Nature biotechnology. Apr. 2000, 18(4):457-459.
Weichhart et al., "Functional selection of vaccine candidate peptides from *Staphylococcus aureus* whole-genome expression libraries in vitro," Infection and Immunity, 2003, 71 (8):4333-4641.
Weinstein et al., "DNA microscopy: Optics-free spatio-genetic imaging by a stand-alone chemical reaction", bioRxiv, 41 pages, 2018.
Willi-Monnerat et al., "Comprehensive spatiotemporal transcriptomic analyses of the ganglionic eminences demonstrate the uniqueness of its caudal subdivision," Molecular and Cellular Nueorsciences 37: 845-856, 2008.
Wolf et al., "Rapid hybridization kinetics of DNA attached to submicron latex particles", Nucleic Acids Res. 15: 2911-2926, 1987.
Wong et al., "Direct Site-Selective Covalent Protein Immobilization Catalyzed by a Phosphopantetheinyl Transferase," J. Am. Chem Soc., 2008, 130:12456-64.
Woo et al., "A Comparison of cDNA, Oligonucleotide, and Affymetrix GeneChip Gene Expression Microarray Platforms," Journal of Biomolecular Techniques, 2004, 15(4), 276-284.
Worthington et al., "Cloning of random oligonucleotides to create single-insert plasmid libraries," Analyt. Biochem, 2001, 294:169-175.
Xiao et al., "Direct determination of haplotypes from single DNA molecules," Nature Methods, 2009, 6(3):199-01.
Yin et al., "Genetically encoded short peptide tag for versatile protein labeling by Sfp phosphopantetheinyl transferase," PNAS, 2005, 102(44):15815-20.
Yonezawa et al., "DNA display for in vitro selection of diverse peptide libraries," Nucleic Acids Research, 2003, 31 (19):e118.
Zhang et al., "Assembling DNA through Affinity Binding to Achieve Ultrasensitive Protein Detection," Anaew Chem Int Ed (2013) 52:2-10.
Zhang et al., "Binding-induced DNA assembly and its application to yoctomole detection of proteins," Anal Chem (2012) 84(2):877-884.
Zheng et al., Origins of human mitochondrial point mutations as DNA polymerase mediated errors. Mutat. Res. 599(1-2): 11-20, 2006.
Zhou et al., "Genetically Encoded Short Peptide Tags for Orthogonal Protein Labeling by Sfp and Ac S Phos ho entethein I Transferases," ACS Chemical Biolo 2007 2 5 : 337-346.
Zilberman et al., "Genome-wide analysis of DNA methylation patterns," Development (2007) 134: 3959-3965.
Zlobec et al., "Next-generation tissue microarray (ngTMA) increases the quality of biomarker studies: an example using CD3, CD8, and CD45RO in the tumor microenvironment of six different solid tumor t es," Journal of Translational Medicine 2013 11:104.

(56) References Cited

OTHER PUBLICATIONS

Chen et al., "ATAC-see reveals the accessible genome by transposase-mediated imaging and sequencing," Nature Methods, Dec. 2016, 13(12):1013-1024.

Corces et al., "Lineage-specific and single-cell chromatin accessibility charts human hematopoiesis and leukemia evolution," nature genetics, Oct. 2016, 48(10):1193-1206.

Stahl et al., "Visualization and analysis of gene expression in tissue sections by spatial transcriptomics," Science 353, 78-82, Jun. 30, 2016.

Bullard et al., "Direct comparison of nick-joining activity of the nucleic acid ligases from bacteriophage T4," Biochem. J. 2006, 398:135-144.

U.S. Appl. No. 60/416,118 Fan et al., Multiplex Nucleic Acid Analysis Using Archived or Fixed Samples, filed Oct. 3, 2002, 22 pages.

Cornett et al., "MALDI imaging mass spectrometry: molecular snapshots of biochemical systems," Nature Methods, 2007, 4(10):828-833.

Chung et al., "Structural and molecular interrogation of intact biological systems," Nature, May 16, 2013, 497:332-337.

Schwartz et al., "Capturing native long-range contiguity by in situ library construction and optical sequencing," PNAS, Nov. 13, 2012, 109(46):18749-18754.

Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.

Liu et al., An integrated and sensitive detection platform for biosensing application based on Fe@Au magnetic nanoparticles as bead array carries Biosensors and Bioelectronics, 2010, 26(4):1442-1448.

Sumitomo et al., "$Ca^{2+}$ ion transport through channels formed by -hemolysin analyzed using a microwell array on a Si substrate," Biosensors and Bioelectronics, 2012, 31(1):445-450.

Wu et al., "Detection DNA Point Mutation with Rolling-Circle Amplification Chip," Bioinformatics and Biomedical Engineering (ICBBE), 2010 4th International Conference on IEEE, Piscatway, NJ, USA, Jun. 18, 2010, 1-4 pages.

\* cited by examiner

A

B

A

B

← Phi X

BODT-1 library

← Phi X

| Lane | Tiles | Density (K/mm2) | Clusters PF (%) | Phas/Prephas (%) | Reads (M) | Reads PF (M) | % >= Q30 |
|---|---|---|---|---|---|---|---|
| 1) Phi X | 21 | 904 +/- 62 | 92.1 +/- 1.0 | 0.797 / 0.097 | 9.83 | 9.06 | 94.6 |
| 2) 3.2 nM BODT -1 | 21 | 1026 +/- 171 | 48.2 +/- 36.6 | 0.948 / 0.151 | 11.15 | 5.59 | 72.9 |
| 3) 3.2 nM BODT -1 | 21 | 975 +/- 186 | 41.9 +/- 43.2 | 0.964 / 0.154 | 10.6 | 5.03 | 70.8 |
| 4) 3.2 nM BODT -1 | 21 | 1144 +/- 24 | 85.3 +/- 14.3 | 0.969 / 0.163 | 12.45 | 10.62 | 76.4 |
| 5) 3.2 nM BODT -1 | 21 | 1136 +/- 37 | 90.6 +/- 0.8 | 0.977 / 0.173 | 12.35 | 11.19 | 80.5 |
| 6) 3.2 nM BODT -1 | 21 | 1128 +/- 28 | 90.5 +/- 0.7 | 0.953 / 0.182 | 12.27 | 11.1 | 80.6 |
| 7) 3.2 nM BODT -1 | 21 | 1131 +/- 28 | 90.3 +/- 0.8 | 0.955 / 0.170 | 12.3 | 11.1 | 82.6 |
| 8) Phi X | 21 | 763 +/- 41 | 91.3 +/- 0.4 | 0.756 / 0.135 | 8.3 | 7.58 | 94 |

A

B

A

B

A

B

SPATIALLY DISTINGUISHED, MULTIPLEX NUCLEIC ACID ANALYSIS OF BIOLOGICAL SPECIMENS

CROSS-REFERENCE TO RELATED APPLICATIONS

The present application is a 371 of International Application No. PCT/EP2016/057355, filed on Apr. 6, 2016, which claims the benefit of U.S. Provisional Application No. 62/145,874.

BACKGROUND

One of every four men will die of cancer. Further statistics from the American Cancer Society predict that one of every five women will suffer the same fate. Treatments are available for many cancers. However, success for most relies on early detection.

Cancer is now said to be a disease of the genome. Many oncologists and cancer researchers hope that advances in genomic analysis tools will provide early detection and a path to treatment. However, these tools are more prominent in research labs having not yet matured to the level of being readily available to the vast majority of oncologists. Improvements are needed.

It has been said that at the time of diagnosis, all cancer patients are mosaics. They are mosaics because they have at least two distinct genomes: the genome they were born with, and the genome that they unwillingly acquired via cancer. Furthermore, as tumors grow, distinct populations of cancer cells become apparent. Leading to even more complex mosaics within the tumor. This cancer cell heterogeneity often results in subpopulations of cells that respond differently to cancer therapies. The end result is often an initial positive response of one subpopulation of cells, resulting in the observation of the patient's tumor shrinking, only to be followed by regrowth of tumor tissue, and in some cases metastasis. Despite early detection of the tumor, an inability to identify the subpopulation of cells that are resistant to the treatment can result in loss of time needed to treat an aggressive cancer. This creates adverse consequences for the patient both emotionally and physically.

There is a need for genomic tools that can distinguish subpopulations of cancer cells in tumors. The present disclosure addresses this need and provides other advantages as well.

BRIEF SUMMARY

The present disclosure provides a method for spatially tagging nucleic acids of a biological specimen. The method can include steps of (a) providing a solid support comprising a plurality of different nucleic acid probes that are randomly located on the solid support, wherein the different nucleic acid probes each includes a barcode sequence that is different from the barcode sequence of other randomly located probes on the solid support; (b) performing a nucleic acid detection reaction on the solid support to locate the barcode sequences on the solid support; (c) contacting a biological specimen with the solid support that has the randomly located probes; (d) hybridizing the randomly located probes to target nucleic acids from portions of the biological specimen that are proximal to the randomly located probes; and (e) modifying the randomly located probes that are hybridized to the target nucleic acids, thereby producing modified probes that include the barcode sequences and a target specific modification, thereby spatially tagging the nucleic acids of the biological specimen.

This disclosure further provides a method for spatially tagging nucleic acids of a biological specimen, the method including steps of (a) attaching different nucleic acid probes to a solid support to produce randomly located probes on the solid support, wherein the different nucleic acid probes each includes a barcode sequence, and wherein each of the randomly located probes includes different barcode sequences from other randomly located probes on the solid support; (b) performing a nucleic acid detection reaction on the solid support to determine the barcode sequences of the randomly located probes on the solid support; (c) contacting a biological specimen with the solid support that has the randomly located probes; (d) hybridizing the randomly located probes to target nucleic acids from portions of the biological specimen that are proximal to the randomly located probes; and (e) extending the randomly located probes to produce extended probes that include the barcode sequences and sequences from the target nucleic acids, thereby spatially tagging the nucleic acids of the biological specimen.

Also provided is a method for spatially tagging nucleic acids of a biological specimen that includes the steps of (a) providing a plurality of nucleic acid primers attached to a solid support, wherein the nucleic acid primers in the plurality include a universal primer sequence that is common to the nucleic acid primers in the plurality; (b) binding a population of nucleic acid probes to the plurality of nucleic acid primers, wherein the nucleic acid probes include a universal primer binding sequence that hybridizes to the universal primer sequence, a target capture sequence and a barcode sequence that differs from barcode sequences of other nucleic acid probes in the population, thereby attaching the different nucleic acid probes at randomly located positions on the solid support; (c) amplifying the different nucleic acid probes by extension of the nucleic acid primers, thereby producing nucleic acid clusters having copies of the barcode sequence and target capture sequence at the randomly located positions on the solid support; (d) performing a sequencing reaction to determine the barcode sequences at the randomly located positions on the solid support; (e) contacting a biological specimen with the nucleic acid clusters on the solid support; (f) hybridizing the target capture sequences of the clusters to target nucleic acids from portions of the biological specimen that are proximal to the clusters; and (g) extending the target capture sequences to produce extended probes that include sequences from the target nucleic acids and the copies of the barcode sequences, thereby tagging the nucleic acids of the biological specimen.

This disclosure further provides a method for spatially tagging nucleic acids of a biological specimen, the method including steps of (a) providing an array of beads on a solid support, wherein different nucleic acid probes are attached to different beads in the array, wherein the different nucleic acid probes each include a barcode sequence, wherein each bead includes a different barcode sequence from other beads on the solid support, and wherein each of the different nucleic acid probes includes a target capture sequence; (b) performing a decoder probe hybridization reaction on the solid support to determine the barcode sequences at the randomly located probes on the solid support; (c) contacting a biological specimen with the array of beads; (d) hybridizing the different nucleic acid probes to target nucleic acids from portions of the biological specimen that are proximal to the beads; and (e) extending the different nucleic acid probes to produce extended probes that include sequences from the target nucleic acids and the barcode sequences, thereby tagging the nucleic acids of the biological specimen.

BRIEF DESCRIPTION OF THE DRAWINGS

FIG. 3 shows sequencing metrics of the flow cell described in Example 1 and shown in FIG. 2.

DETAILED DESCRIPTION

Figure 1:
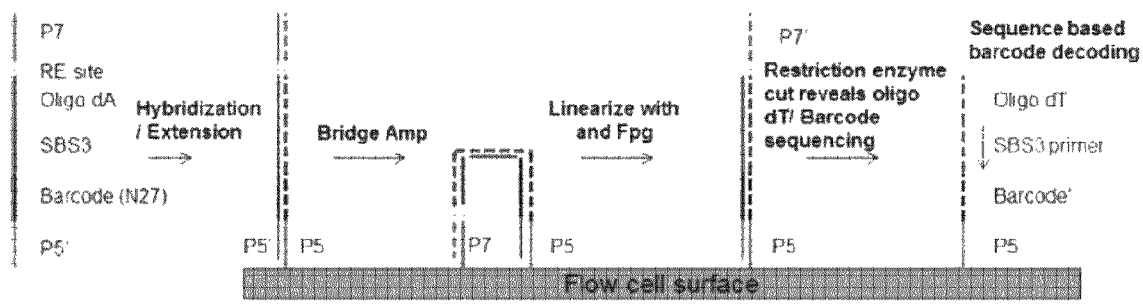
FIG. 1 shows a diagrammatic representation of steps and reagents that can be used to generate barcoded oligo dT probes on an Illumina flow cell, create extended barcoded probes having mRNA sequences and releasing the extended probes from the flow cell.
Figure 1:
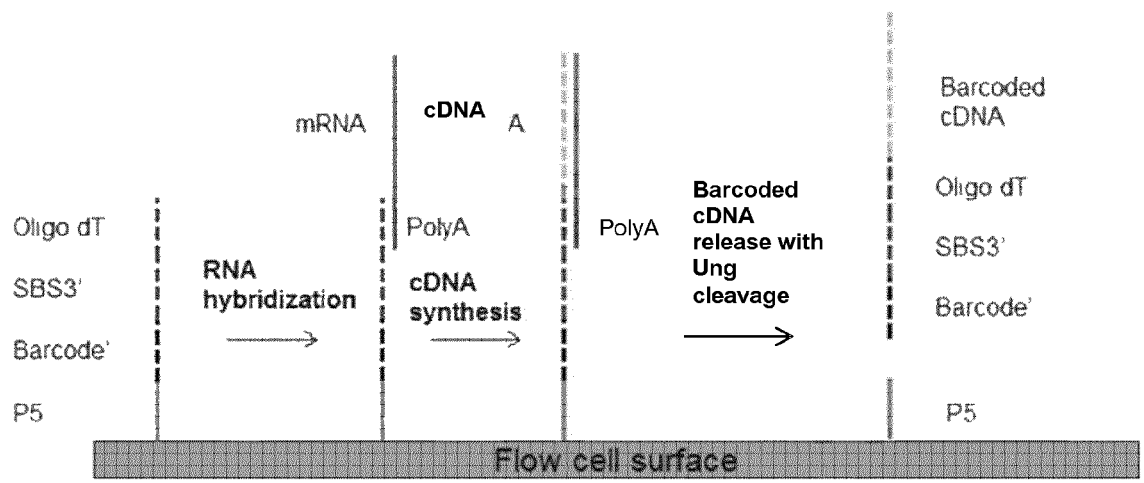

The present disclosure provides compositions, apparatus and methods for preserving spatial information when performing multiplex nucleic acid analyses of biological specimens. A variety of tools are available for multiplex nucleic acid analyses including, for example, nucleic acid microarrays and so-called "next generation" sequencing platforms. Such tools allow for parallel detection of very large and complex collections of nucleic acids, including for example, DNA collections that represent all or nearly all of the genetic material of an organism (i.e. the 'genome'), RNA (or cDNA) collections that represent all or nearly all of the complement of expressed genes (i.e. the 'transcriptome') for an organism, and in some cases the collections can include several genomes and/or transcriptomes from several different organisms (e.g. a metabolome or biome from a community or ecosystem). Although these tools provide a vast amount of information about what nucleic acid sequences are present in a biological specimen being evaluated, they do not inherently distinguish where any particular nucleic acid resided in the biological specimen. Indeed the vast majority of samples applied to multiplex nucleic acid analysis tools are homogenates derived from mixtures of many different cells from a biological specimen. As a result, spatial information is lost and the results obtained from these tools constitute an average transcriptome or average genome for the specimen, important differences between individual cells being lost.

In particular embodiments, the present disclosure provides new and useful modifications to existing multiplex nucleic acid analysis tools to allow for the preservation of spatial information for biological specimens from which the nucleic acids are obtained. For example, solid supports that are usually used for multiplex sequencing-by-synthesis (SBS) techniques can be modified for use in capturing and spatially tagging nucleic acids from a biological specimen. In an alternative example, arrays of beads, such as those used for genotyping or gene expression analysis, can be used for capturing and spatially tagging nucleic acids from a biological specimen. As set forth in examples below, the solid supports used for an SBS or BeadArray™ platform commercialized by Illumina (San Diego, Calif.) can be modified for spatial tagging. However, it will be understood that any of a variety of solid supports can be made and used in accordance with the teaching herein. The spatially tagged nucleic acids can be removed from the solid support, pooled together and attached to a second solid support for detection in any of a variety of multiplex nucleic acid analysis systems including, for example, a sequencing platform or microarray platform set forth herein.

The spatial information provided by a method, composition or apparatus herein can include, for example, the location of one or more cells in a tissue (or other specimen) that has a particular allele at one or more locus (e.g. a genotype), has a particular structural variation in the genome (e.g. fusion, insertion, deletion, rearrangement etc.), has a particular epigenetic signature (e.g. methylation), expresses a particular gene, expresses a particular allele of a gene, expresses a particular splice variant of a gene or the like. In addition to identifying nucleic acids according to their spatial location in a biological specimen, a method, composition or apparatus of the present disclosure can be used to quantify one or more nucleic acids according to spatial location. For example, the spatial information for one or more cells in a tissue (or other specimen) can include the amount of a particular allele or chromosomal region in a genome (e.g. ploidy); the amount of epigenetic modification of a genetic locus (e.g. methylation); expression level for a particular gene, allele or splice variant; or the like. The amounts can be absolute amounts or relative amounts in accordance with similar measurements obtained in the art for mixed or non-spatially tagged samples.

A method set forth herein can be used for localized detection of a nucleic acid in a biological specimen. In some embodiments, a method can be used for identifying or characterizing all of the transcriptome or genome of a biological specimen. Alternatively, a method can be used to identify or characterize only a part of a specimen's transcriptome or genome. A subset of transcripts or genes evaluated in a method herein can be related to a particular disease or condition.

A method set forth herein can be used for localized or spatial detection of nucleic acids, whether DNA or RNA, in a biological specimen. Thus one or more RNA or DNA molecules can be located with respect to its native position or location within a cell or tissue or other biological specimen. For example, one or more nucleic acids can be localized to a cell or group of adjacent cells, or type of cell, or to particular regions of areas within a tissue sample. The native location or position of individual RNA or DNA molecules can be determined using a method, apparatus or composition of the present disclosure.

Terms used herein will be understood to take on their ordinary meaning in the relevant art unless specified otherwise. Several terms used herein and their meanings are set forth below.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), multiple displacement amplification (MDA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "array" refers to a population of features or sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "attached" refers to the state of two things being joined, fastened, adhered, connected or bound to each other. For example, an analyte, such as a nucleic acid, can be attached to a material, such as a gel or solid support, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "barcode sequence" is intended to mean a series of nucleotides in a nucleic acid that can be used to identify the nucleic acid, a characteristic of the nucleic acid, or a manipulation that has been carried out on the nucleic acid. The barcode sequence can be a naturally occurring sequence or a sequence that does not occur naturally in the organism from which the barcoded nucleic acid was obtained. A barcode sequence can be unique to a single nucleic acid species in a population or a barcode sequence can be shared by several different nucleic acid species in a population. For example, each nucleic acid probe in a population can include different barcode sequences from all other nucleic acid probes in the population. Alternatively, each nucleic acid probe in a population can include different barcode sequences from some or most other nucleic acid probes in a population. For example, each probe in a population can have a barcode that is present for several different probes in the population even though the probes with the common barcode differ from each other at other sequence regions along their length. In particular embodiments, one or more barcode sequences that are used with a biological specimen are not present in the genome, transcriptome or other nucleic acids of the biological specimen. For example, barcode sequences can have less than 80%, 70%, 60%, 50% or 40% sequence identity to the nucleic acid sequences in a particular biological specimen.

As used herein, the term "biological specimen" is intended to mean one or more cell, tissue, organism or portion thereof. A biological specimen can be obtained from any of a variety of organisms. Exemplary organisms include, but are not limited to, a mammal such as a rodent, mouse, rat, rabbit, guinea pig, ungulate, horse, sheep, pig, goat, cow, cat, dog, primate (i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii*, *Takifugu rubripes*, yeast, *Saccharamoyces cerevisiae* or *Schizosaccharomyces pombe*; or a Plasmodium falciparum. Target nucleic acids can also be derived from a prokaryote such as a bacterium, *Escherichia coli*, Staphylococci or *Mycoplasma pneumoniae*; an archae; a virus such as Hepatitis C virus or human immunodeficiency virus; or a viroid. Specimens can be derived from a homogeneous culture or population of the above organisms or alternatively from a collection of several different organisms, for example, in a community or ecosystem.

As used herein, the term "cleavage site" is intended to mean a location in a nucleic acid molecule that is susceptible to bond breakage. The location can be specific to a particular chemical, enzymatic or physical process that results in bond breakage. For example, the location can be a nucleotide that is abasic or a nucleotide that has a base that is susceptible to being removed to create an abasic site. Examples of nucleotides that are susceptible to being removed include uracil and 8-oxo-guanine as set forth in further detail herein below. The location can also be at or near a recognition sequence for a restriction endonuclease such as a nicking enzyme.

As used herein, the term "cluster," when used in reference to nucleic acids, refers to a population of the nucleic acids that is attached to a solid support to form a feature or site. The nucleic acids are generally members of a single species, thereby forming a monoclonal cluster. A "monoclonal population" of nucleic acids is a population that is homogeneous with respect to a particular nucleotide sequence. Clusters need not be monoclonal. Rather, for some applications, a cluster can be predominantly populated with amplicons from a first nucleic acid and can also have a low level of contaminating amplicons from a second nucleic acid. For example, when an array of clusters is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual cluster include, but are not limited to, at most 0.1%, 0.5%, 1%, 5%, 10%, 5 25%, or 35% contaminating amplicons. The nucleic acids in a cluster are generally covalently attached to a solid support, for example, via their 5' ends, but in some cases other attachment means are possible. The nucleic acids in a cluster can be single stranded or double stranded. In some but not all embodiments, clusters are made by a solid-phase amplification method known as bridge amplification. Exemplary configurations for clusters and methods for their production are set forth, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different for the two or more molecules while also having a universal sequence portion that is the same on the two or more molecules. Two beads can be different from each other by virtue of being attached to different nucleic acids.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "extend," when used in reference to a nucleic acid, is intended to mean addition of at least one nucleotide or oligonucleotide to the nucleic acid. In particular embodiments one or more nucleotides can be added to the 3' end of a nucleic acid, for example, via polymerase catalysis (e.g. DNA polymerase, RNA polymerase or reverse transcriptase). Chemical or enzymatic methods can be used to add one or more nucleotide to the 3' or 5' end of a nucleic acid. One or more oligonucleotides can be added to the 3' or 5' end of a nucleic acid, for example, via chemical or enzymatic (e.g. ligase catalysis) methods. A nucleic acid can be extended in a template directed manner, whereby the product of extension is complementary to a template nucleic acid that is hybridized to the nucleic acid that is extended.

As used herein, the term "feature" means a location in an array for a particular species of molecule. A feature can contain only a single molecule or it can contain a population of several molecules of the same species. Features of an array are typically discrete. The discrete features can be contiguous or they can have spaces between each other. The size of the features and/or spacing between the features can vary such that arrays can be high density, medium density or lower density. High density arrays are characterized as having sites separated by less than about 15 µm. Medium density arrays have sites separated by about 15 to 30 µm, while low density arrays have sites separated by greater than 30 µm. An array useful herein can have, for example, sites that are separated by less than 100 µm, 50 µm, 10 µm, 5 µm, 1 µm, or 0.5 µm. An apparatus or method of the present disclosure can be used to detect an array at a resolution sufficient to distinguish sites at the above densities or density ranges.

As used herein, the term "fluidic mixture" is intended to mean two or more different items that are simultaneously present in a solution. Typically, the two or more items are freely diffusible in the solution. The two or more items can be different types of items (e.g. a nucleic acid and a protein which are different types of molecules) or they can be different species of the same type of items (e.g. two nucleic acid molecules having different sequences). Exemplary items that can be in a fluidic mixture include, but are not limited to, molecules, cells or beads.

As used herein, the term "flow cell" is intended to mean a vessel having a chamber where a reaction can be carried out, an inlet for delivering reagents to the chamber and an outlet for removing reagents from the chamber. In some embodiments the chamber is configured for detection of the reaction that occurs in the chamber. For example, the chamber can include one or more transparent surfaces allowing optical detection of biological specimens, optically labeled molecules, or the like in the chamber. Exemplary flow cells include, but are not limited to those used in a nucleic acid sequencing apparatus such as flow cells for the Genome Analyzer®, MiSeq®, NextSeq® or HiSeq® platforms commercialized by Illumina, Inc. (San Diego, Calif.); or for the SOLiD™ or Ion Torrent™ sequencing platform commercialized by Life Technologies (Carlsbad, Calif.). Exemplary flow cells and methods for their manufacture and use are also described, for example, in WO 2014/142841 A1; U.S. Pat. App. Pub. No. 2010/0111768 A1 and U.S. Pat. No. 8,951,781, each of which is incorporated herein by reference.

As used herein, the term "gel" is intended to mean a semi-rigid material that is permeable to liquids and gases. Typically, gel material can swell when liquid is taken up and can contract when liquid is removed by drying. Exemplary gels include, but are not limited to those having a colloidal structure, such as agarose; polymer mesh structure, such as gelatin; or cross-linked polymer structure, such as polyacrylamide, SFA (see, for example, US Pat. App. Pub. No. 2011/0059865 A1, which is incorporated herein by reference) or PAZAM (see, for example, US Pat. App. Publ. No. 2014/0079923 A1, which is incorporated herein by reference). Particularly useful gel material will conform to the shape of a well or other concave feature where it resides.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid or sequence of a nucleic acid, are intended as semantic identifiers for the nucleic acid or sequence in the context of a method or composition set forth herein and does not necessarily limit the structure or function of the nucleic acid or sequence beyond what is otherwise explicitly indicated. The terms "probe" and "target" can be similarly applied to other analytes such as proteins, small molecules, cells or the like.

As used herein, the term "pitch," when used in reference to features of an array, is intended to refer to the center-to-center spacing for adjacent features. A pattern of features can be characterized in terms of average pitch. The pattern can be ordered such that the coefficient of variation around the average pitch is small or the pattern can be random in which case the coefficient of variation can be relatively large. In either case, the average pitch can be, for example, at least about 10 nm, 0.1 µm, 0.5 µm, 1 µm, 5 µm, 10 µm, 100 µm or more. Alternatively or additionally, the average pitch can be, for example, at most about 100 µm, 10 µm, 5 µm, 1 µm, 0.5 µm 0.1 µm or less. Of course, the average pitch for a particular pattern of features can be between one of the lower values and one of the upper values selected from the ranges above.

As used herein, the term "poly T or poly A," when used in reference to a nucleic acid sequence, is intended to mean a series of two or more thiamine (T) or adenine (A) bases, respectively. A poly T or poly A can include at least about 2, 5, 8, 10, 12, 15, 18, 20 or more of the T or A bases, respectively. Alternatively or additionally, a poly T or poly A can include at most about, 30, 20, 18, 15, 12, 10, 8, 5 or 2 of the T or A bases, respectively.

As used herein, the term "random" can be used to refer to the spatial arrangement or composition of locations on a surface. For example, there are at least two types of order for an array described herein, the first relating to the spacing and relative location of features (also called "sites") and the second relating to identity or predetermined knowledge of the particular species of molecule that is present at a particular feature. Accordingly, features of an array can be randomly spaced such that nearest neighbor features have variable spacing between each other. Alternatively, the spacing between features can be ordered, for example, forming a regular pattern such as a rectilinear grid or hexagonal grid. In another respect, features of an array can be random with respect to the identity or predetermined knowledge of the species of analyte (e.g. nucleic acid of a particular sequence) that occupies each feature independent of whether spacing produces a random pattern or ordered pattern. An array set forth herein can be ordered in one respect and random in another. For example, in some embodiments set forth herein a surface is contacted with a population of nucleic acids under conditions where the nucleic acids attach at sites that are ordered with respect to their relative locations but 'randomly located' with respect to knowledge of the sequence for the nucleic acid species present at any particular site. Reference to "randomly distributing" nucleic acids at locations on a surface is intended to refer to the absence of knowledge or absence of predetermination regarding which nucleic acid will be captured at which location (regardless of whether the locations are arranged in an ordered pattern or not).

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful solid supports for some embodiments are located within a flow cell apparatus. Exemplary flow cells are set forth in further detail herein.

As used herein, the term "spatial tag" is intended to mean a nucleic acid having a sequence that is indicative of a location. Typically, the nucleic acid is a synthetic molecule having a sequence that is not found in one or more biological specimen that will be used with the nucleic acid. However, in some embodiments the nucleic acid molecule can be naturally derived or the sequence of the nucleic acid can be naturally occurring, for example, in a biological specimen that is used with the nucleic acid. The location indicated by a spatial tag can be a location in or on a biological specimen, in or on a solid support or a combination thereof. A barcode sequence can function as a spatial tag.

As used herein, the term "tissue" is intended to mean an aggregation of cells, and, optionally, intercellular matter. Typically the cells in a tissue are not free floating in solution and instead are attached to each other to form a multicellular structure. Exemplary tissue types include muscle, nerve, epidermal and connective tissues.

As used herein, the term "universal sequence" refers to a series of nucleotides that is common to two or more nucleic acid molecules even if the molecules also have regions of sequence that differ from each other. A universal sequence that is present in different members of a collection of molecules can allow capture of multiple different nucleic acids using a population of universal capture nucleic acids that are complementary to the universal sequence. Similarly, a universal sequence present in different members of a collection of molecules can allow the replication or amplification of multiple different nucleic acids using a population of universal primers that are complementary to the universal sequence. Thus, a universal capture nucleic acid or a universal primer includes a sequence that can hybridize specifically to a universal sequence. Target nucleic acid molecules may be modified to attach universal adapters, for example, at one or both ends of the different target sequences.

The embodiments set forth below and recited in the claims can be understood in view of the above definitions.

The present disclosure provides a method for spatially tagging nucleic acids of a biological specimen. The method can include the steps of (a) attaching different nucleic acid probes to a solid support to produce randomly located probes on the solid support, wherein the different nucleic acid probes each includes a barcode sequence, and wherein each of the randomly located probes includes different barcode sequences from other randomly located probes on the solid support; (b) performing a nucleic acid detection reaction on the solid support to determine the barcode sequences of the randomly located probes on the solid support; (c) contacting a biological specimen with the solid support that has the randomly located probes; (d) hybridizing the randomly located probes to target nucleic acids from portions of the biological specimen that are proximal to the randomly located probes; and (e) extending the randomly located probes to produce extended probes that include the barcode sequences and sequences from the target nucleic acids, thereby spatially tagging the nucleic acids of the biological specimen.

Any of a variety of solid supports can be used in a method, composition or apparatus of the present disclosure. Particularly useful solid supports are those used for nucleic acid arrays. Examples include glass, modified glass, functionalized glass, inorganic glasses, microspheres (e.g. inert and/or magnetic particles), plastics, polysaccharides, nylon, nitrocellulose, ceramics, resins, silica, silica-based materials, carbon, metals, an optical fiber or optical fiber bundles, polymers and multiwell (e.g. microtiter) plates. Exemplary plastics include acrylics, polystyrene, copolymers of styrene and other materials, polypropylene, polyethylene, polybutylene, polyurethanes and Teflon™. Exemplary silica-based materials include silicon and various forms of modified silicon.

In particular embodiments, a solid support can be within or part of a vessel such as a well, tube, channel, cuvette, Petri plate, bottle or the like. A particularly useful vessel is a flow-cell, for example, as described in WO 2014/142841 A1; U.S. Pat. App. Pub. No. 2010/0111768 A1 and U.S. Pat. No. 8,951,781 or Bentley et al., *Nature* 456:53-59 (2008), each of which is incorporated herein by reference. Exemplary flow-cells are those that are commercially available from Illumina, Inc. (San Diego, Calif.) for use with a sequencing platform such as a Genome Analyzer®, MiSeq®, NextSeq® or HiSeq® platform. Another particularly useful vessel is a well in a multiwell plate or microtiter plate.

Optionally, a solid support can include a gel coating. Attachment of nucleic acids to a solid support via a gel is exemplified by flow cells available commercially from Illumina Inc. (San Diego, Calif.) or described in US Pat. App. Pub. Nos. 2011/0059865 A1, 2014/0079923 A1, or 2015/0005447 A1; or PCT Publ. No. WO 2008/093098, each of which is incorporated herein by reference. Exemplary gels that can be used in the methods and apparatus set forth herein include, but are not limited to, those having a colloidal structure, such as agarose; polymer mesh structure, such as gelatin; or cross-linked polymer structure, such as polyacrylamide, SFA (see, for example, US Pat. App. Pub. No. 2011/0059865 A1, which is incorporated herein by reference) or PAZAM (see, for example, US Pat. App. Publ. Nos. 2014/0079923 A1, or 2015/0005447 A1, each of which is incorporated herein by reference).

In some embodiments, a solid support can be configured as an array of features to which nucleic acids can be attached. The features can be present in any of a variety of desired formats. For example, the features can be wells, pits, channels, ridges, raised regions, pegs, posts or the like. In some embodiments, the features can contain beads. However, in particular embodiments the features need not contain a bead or particle. Exemplary features include wells that are present in substrates used for commercial sequencing platforms sold by 454 LifeSciences (a subsidiary of Roche, Basel Switzerland) or Ion Torrent (a subsidiary of Life Technologies, Carlsbad Calif.). Other substrates having wells include, for example, etched fiber optics and other substrates described in U.S. Pat. Nos. 6,266,459; 6,355,431; 6,770,441; 6,859,570; 6,210,891; 6,258,568; 6,274,320; US Pat app. Publ. Nos. 2009/0026082 A1; 2009/0127589 A1; 2010/0137143 A1; 2010/0282617 A1 or PCT Publication No. WO 00/63437, each of which is incorporated herein by reference. In some embodiments, wells of a substrate can include gel material (with or without beads) as set forth in US Pat. App. Publ. No. 2014/0243224 A1, which is incorporated herein by reference.

The features on a solid support can be metal features on a non-metallic surface such as glass, plastic or other materials exemplified above. A metal layer can be deposited on a surface using methods known in the art such as wet plasma etching, dry plasma etching, atomic layer deposition, ion beam etching, chemical vapor deposition, vacuum sputtering or the like. Any of a variety of commercial instruments can be used as appropriate including, for example, the FlexAL®, OpAL®, Ionfab 300Plus®, or Optofab 3000® systems (Oxford Instruments, UK). A metal layer can also be deposited by e-beam evaporation or sputtering as set forth in Thornton, *Ann. Rev. Mater. Sci.* 7:239-60 (1977), which is incorporated herein by reference. Metal layer deposition techniques, such as those exemplified above, can be combined with photolithography techniques to create metal regions or patches on a surface. Exemplary methods for combining metal layer deposition techniques and photolithography techniques are provided in U.S. Pat. No. 8,895,249 or US Pat App. Pub. No. 2014/0243224 A1, each of which is incorporated herein by reference.

Features can appear on a solid support as a grid of spots or patches. The features can be located in a repeating pattern or in an irregular, non-repeating pattern. Particularly useful repeating patterns are hexagonal patterns, rectilinear patterns, grid patterns, patterns having reflective symmetry, patterns having rotational symmetry, or the like. Asymmetric patterns can also be useful. The pitch can be the same between different pairs of nearest neighbor features or the pitch can vary between different pairs of nearest neighbor features.

High density arrays are characterized as having average pitch of less than about 15 µm. Medium density arrays have average pitch of about 15 to 30 µm, while low density arrays have average pitch greater than 30 µm. An array useful in the invention can have average pitch that is less than 100 µm, 50 µm, 10 µm, 5 µm, 1 µm or 0.5 µm. The average pitch values and ranges set forth above or elsewhere herein are intended to be applicable to ordered arrays or random arrays.

In particular embodiments, features on a solid support can each have an area that is larger than about 100 nm$^2$, 250 nm$^2$, 500 nm$^2$, 1 µm$^2$, 2.5 µm$^2$, 5 µm$^2$, 10 µm$^2$, 100 µm$^2$, or 500 µm$^2$. Alternatively or additionally, features can each have an area that is smaller than about 1 mm$^2$, 500 µm$^2$, 100 µm$^2$, 25 µm2, 10 µm$^2$, 5 µm$^2$, 1 µm$^2$, 500 nm$^2$, or 100 nm$^2$. The above ranges can describe the apparent area of a bead or other particle on a solid support when viewed or imaged from above.

In particular embodiments, a solid support can include a collection of beads or other particles. The particles can be suspended in a solution or they can be located on the surface of a substrate. Examples of arrays having beads located on a surface include those wherein beads are located in wells such as a BeadChip array (Illumina Inc., San Diego Calif.), substrates used in sequencing platforms from 454 LifeSciences (a subsidiary of Roche, Basel Switzerland) or substrates used in sequencing platforms from Ion Torrent (a subsidiary of Life Technologies, Carlsbad Calif.). Other solid supports having beads located on a surface are described in U.S. Pat. No. 6,266,459; 6,355,431; 6,770,441; 6,859,570; 6,210,891; 6,258,568; or 6,274,320; US Pat. App. Publ. Nos. 2009/0026082 A1; 2009/0127589 A1; 2010/0137143 A1; or 2010/0282617 A1 or PCT Publication No. WO 00/63437, each of which is incorporated herein by reference. Several of the above references describe methods for attaching nucleic acid probes to beads prior to loading the beads in or on a solid support. As such, the collection of beads can include different beads each having a unique probe attached. It will however, be understood that the beads can be made to include universal primers, and the beads can then be loaded onto an array, thereby forming universal arrays for use in a method set forth herein. As set forth previously herein, the solid supports typically used for bead arrays can be used without beads. For example, nucleic acids, such as probes or primers can be attached directly to the wells or to gel material in wells. Thus, the above references are illustrative of materials, compositions or apparatus that can be modified for use in the methods and compositions set forth herein.

Accordingly, a solid support used in a method set forth herein can include an array of beads, wherein different nucleic acid probes are attached to different beads in the array. In this embodiment, each bead can be attached to a different nucleic acid probe and the beads can be randomly distributed on the solid support in order to effectively attach the different nucleic acid probes to the solid support. Optionally, the solid support can include wells having dimensions that accommodate no more than a single bead. In such a configuration, the beads may be attached to the wells due to forces resulting from the fit of the beads in the wells. It is also possible to use attachment chemistries or adhesives to hold the beads in the wells.

Nucleic acid probes that are attached to beads can include barcode sequences. A population of the beads can be configured such that each bead is attached to only one type of barcode and many different beads each with a different barcode are present in the population. In this embodiment, randomly distributing the beads to a solid support will result in randomly locating the nucleic acid probes (and their respective barcode sequences) on the solid support. In some cases there can be multiple beads with the same barcode sequence such that there is redundancy in the population. Randomly distributing a redundant population of beads on a solid support that has a capacity that is greater than the number of unique barcodes in the bead population will result in redundancy of barcodes on the solid support. Alternatively, the number of different barcodes in a population of beads can exceed the capacity of the solid support in order to produce an array that is not redundant with respect to the population of barcodes on the solid support. The capacity of the solid support will be determined in some embodiments by the number of features (e.g. single-bead occupancy wells) that attach or otherwise accommodate a bead.

A solid support can include, or can be made by the methods set forth herein to attach, a plurality of different nucleic acid probes. For example, a solid support can include at least 10, 100, $1 \times 10^3$, $1 \times 10^4$, $1 \times 10^5$, $1 \times 10^6$, $1 \times 10^7$, $1 \times 10^8$, $1 \times 10^9$ or more different probes. Alternatively or additionally, a solid support can include at most $1 \times 10^9$, $1 \times 10^8$, $1 \times 10^7$, $1 \times 10^6$, $1 \times 10^5$, $1 \times 10^4$, $1 \times 10^3$, 100, or fewer different probes. It will be understood that each of the different probes can be present in several copies, for example, when the probes have been amplified to form a cluster. Thus, the above ranges can describe the number of different nucleic acid clusters on a solid support. It will also be understood that the above ranges can describe the number of different barcodes, target capture sequences, or other sequence elements set forth herein as being unique to particular nucleic acid probes. Alternatively or additionally, the ranges can describe the number of extended probes or modified probes created on a solid support using a method set forth herein.

Features, may be present on a solid support prior to contacting the solid support with nucleic acid probes. For example, in embodiments where probes are attached to a support via hybridization to primers, the primers can be attached at the features, whereas interstitial areas outside of the features substantially lack any of the primers. Nucleic acid probes can be captured at preformed features on a solid support, and optionally amplified on the solid support, using methods set forth in U.S. Pat. Nos. 8,895,249, 8,778,849, or US Pat App. Pub. No. 2014/0243224 A1, each of which is incorporated herein by reference. Alternatively, a solid support may have a lawn of primers or may otherwise lack features. In this case, a feature can be formed by virtue of attachment of a nucleic acid probe on the solid support. Optionally, the captured nucleic acid probe can be amplified on the solid support such that the resulting cluster becomes a feature. Although attachment is exemplified above as capture between a primer and a complementary portion of a probe, it will be understood that capture moieties other than primers can be present at pre-formed features or as a lawn. Other exemplary capture moieties include, but are not limited to, chemical moieties capable of reacting with a nucleic acid probe to create a covalent bond or receptors capable of biding non-covalently to a ligand on a nucleic acid probe.

A step of attaching nucleic acid probes to a solid support can be carried out by providing a fluid that contains a mixture of different nucleic acid probes and contacting this fluidic mixture with the solid support. The contact can result in the fluidic mixture being in contact with a surface to which many different nucleic acid probes from the fluidic mixture will attach. Thus, the probes have random access to the surface (whether the surface has pre-formed features configured to attach the probes or a uniform surface configured for attachment). Accordingly, the probes can be randomly located on the solid support.

The total number and variety of different probes that end up attached to a surface can be selected for a particular application or use. For example, in embodiments where a fluidic mixture of different nucleic acid probes is contacted with a solid support for purposes of attaching the probes to the support, the number of different probe species can exceed the occupancy of the solid support for probes. Thus, the number and variety of different probes that attach to the solid support can be equivalent to the probe occupancy of the solid support. Alternatively, the number and variety of different probe species on the solid support can be less than the occupancy (i.e. there will be redundancy of probe species such that the solid support may contain multiple features having the same probe species). Such redundancy can be achieved, for example, by contacting the solid support with a fluidic mixture that contains a number and variety of probe species that is substantially lower than the probe occupancy of the solid support.

Attachment of the nucleic acid probes can be mediated by hybridization of the nucleic acid probes to complementary primers that are attached to the solid support, chemical bond formation between a reactive moiety on the nucleic acid probe and the solid support (examples are set forth in U.S. Pat. Nos. 8,895,249, 8,778,849, or US Pat App. Pub. No. 2014/0243224 A1, each of which is incorporated herein by reference), affinity interactions of a moiety on the nucleic acid probe with a solid support-bound moiety (e.g. between known receptor-ligand pairs such as streptavidinbiotin, antibody-epitope, lectin-carbohydrate and the like), physical interactions of the nucleic acid probes with the solid support (e.g. hydrogen bonding, ionic forces, van der Waals forces and the like), or other interactions known in the art to attach nucleic acids to surfaces.

In some embodiments, attachment of a nucleic acid probe is non-specific with regard to any sequence differences between the nucleic acid probe and other nucleic acid probes that are or will be attached to the solid support. For example, different probes can have a universal sequence that complements surface-attached primers or the different probes can have a common moiety that mediates attachment to the surface. Alternatively, each of the different probes (or a subpopulation of different probes) can have a unique sequence that complements a unique primer on the solid support or they can have a unique moiety that interacts with one or more different reactive moiety on the solid support. In such cases, the unique primers or unique moieties can, optionally, be attached at predefined locations in order to selectively capture particular probes, or particular types of probes, at the respective predefined locations.

One or more features on a solid support can each include a single molecule of a particular probe. The features can be configured, in some embodiments, to accommodate no more than a single nucleic acid probe molecule. However, whether or not the feature can accommodate more than one nucleic acid probe molecule, the feature may nonetheless include no more than a single nucleic acid probe molecule. Alternatively, an individual feature can include a plurality of nucleic acid probe molecules, for example, an ensemble of nucleic acid probe molecules having the same sequence as each other. In particular embodiments, the ensemble can be produced by amplification from a single nucleic acid probe template to produce amplicons, for example, as a cluster attached to the surface.

A method set forth herein can use any of a variety of amplification techniques. Exemplary techniques that can be used include, but are not limited to, polymerase chain reaction (PCR), rolling circle amplification (RCA), multiple displacement amplification (MDA), or random prime amplification (RPA). In some embodiments the amplification can be carried out in solution, for example, when features of an array are capable of containing amplicons in a volume having a desired capacity. Preferably, an amplification technique used in a method of the present disclosure will be carried out on solid phase. For example, one or more primer species (e.g. universal primers for one or more universal primer binding site present in a nucleic acid probe) can be attached to a solid support. In PCR embodiments, one or both of the primers used for amplification can be attached to a solid support (e.g. via a gel). Formats that utilize two species of primers attached to a solid support are often referred to as bridge amplification because double stranded amplicons form a bridge-like structure between the two surface attached primers that flank the template sequence that has been copied. Exemplary reagents and conditions that can be used for bridge amplification are described, for example, in U.S. Pat. Nos. 5,641,658, 7,115,400, or 8,895,249; or U.S. Pat. Publ. Nos. 2002/0055100 A1, 2004/0096853 A1, 2004/0002090 A1, 2007/0128624 A1 or 2008/0009420 A1, each of which is incorporated herein by reference. Solid-phase PCR amplification can also be carried out with one of the amplification primers attached to a solid support and the second primer in solution. An exemplary format that uses a combination of a surface attached primer and soluble primer is the format used in emulsion PCR as described, for example, in Dressman et al., *Proc. Natl. Acad. Sci. USA* 100:8817-8822 (2003), WO 05/010145, or U.S. Pat. App. Publ. Nos. 2005/0130173 A1 or 2005/0064460 A1, each of which is incorporated herein by reference. Emulsion PCR is illustrative of the format and it will be understood that for purposes of the methods set forth herein the use of an emulsion is optional and indeed for several embodiments an emulsion is not used.

RCA techniques can be modified for use in a method of the present disclosure. Exemplary components that can be used in an RCA reaction and principles by which RCA produces amplicons are described, for example, in Lizardi et al., *Nat. Genet.* 19:225-232 (1998) and US Pat. App. Publ. No. 2007/0099208 A1, each of which is incorporated herein by reference. Primers used for RCA can be in solution or attached to a solid support. The primers can be one or more of the universal primers described herein.

MDA techniques can be modified for use in a method of the present disclosure. Some basic principles and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); U.S. Pat. Nos. 5,455,166; 5,130,238; and 6,214,587, each of which is incorporated herein by reference. Primers used for MDA can be in solution or attached to a solid support at an amplification site. Again, the primers can be one or more of the universal primers described herein.

In particular embodiments a combination of the above-exemplified amplification techniques can be used. For example, RCA and MDA can be used in a combination wherein RCA is used to generate a concatameric amplicon in solution (e.g. using solution-phase primers). The amplicon can then be used as a template for MDA using primers that are attached to a solid support (e.g. universal primers). In this example, amplicons produced after the combined RCA and MDA steps will be attached to the solid support.

Nucleic acid probes that are used in a method set forth herein or present in an apparatus or composition of the present disclosure can include barcode sequences, and for embodiments that include a plurality of different nucleic acid probes, each of the probes can include a different barcode sequence from other probes in the plurality. Barcode sequences can be any of a variety of lengths. Longer sequences can generally accommodate a larger number and variety of barcodes for a population. Generally, all probes in a plurality will have the same length barcode (albeit with different sequences), but it is also possible to use different length barcodes for different probes. A barcode sequence can be at least 2, 4, 6, 8, 10, 12, 15, 20 or more nucleotides in length. Alternatively or additionally, the length of the barcode sequence can be at most 20, 15, 12, 10, 8, 6, 4 or fewer nucleotides. Examples of barcode sequences that can be used are set forth, for example in, US Pat. App. Publ. No. 2014/0342921 A1 and U.S. Pat. No. 8,460,865, each of which is incorporated herein by reference.

A method of the present disclosure can include a step of performing a nucleic acid detection reaction on a solid support to determine barcode sequences of nucleic acid probes that are located on the solid support. In many embodiments the probes are randomly located on the solid support and the nucleic acid detection reaction provides information to locate each of the different probes. Exemplary nucleic acid detection methods include, but are not limited to nucleic acid sequencing of a probe, hybridization of nucleic acids to a probe, ligation of nucleic acids that are hybridized to a probe, extension of nucleic acids that are hybridized to a probe, extension of a first nucleic acid that is hybridized to a probe followed by ligation of the extended nucleic acid to a second nucleic acid that is hybridized to the probe, or other methods known in the art such as those set forth in U.S. Pat. No. 8,288,103 or 8,486,625, each of which is incorporated herein by reference.

Sequencing techniques, such as sequencing-by-synthesis (SBS) techniques, are a particularly useful method for determining barcode sequences. SBS can be carried out as follows. To initiate a first SBS cycle, one or more labeled nucleotides, DNA polymerase, SBS primers etc., can be contacted with one or more features on a solid support (e.g. feature(s) where nucleic acid probes are attached to the solid support). Those features where SBS primer extension causes a labeled nucleotide to be incorporated can be detected. Optionally, the nucleotides can include a reversible termination moiety that terminates further primer extension once a nucleotide has been added to the SBS primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the solid support (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with a composition, apparatus or method of the present disclosure are described, for example, in Bentley et al., *Nature* 456:53-59 (2008), PCT Publ. Nos. WO 91/06678, WO 04/018497 or WO 07/123744; U.S. Pat. No. 7,057,026, 7,329,492, 7,211,414, 7,315,019 or 7,405,281, and US Pat. App. Publ. No. 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); or U.S. Pat. No. 6,210,891, 6,258,568 or 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to apparatus, compositions or methods of the present disclosure are described, for example, in PCT Pat. App. Publ. No. WO2012/058096, US Pat. App. Publ. No. 2005/0191698 A1, or U.S. Pat. No. 7,595,883 or 7,244,559, each of which is incorporated herein by reference.

Sequencing-by-ligation reactions are also useful including, for example, those described in Shendure et al. *Science* 309:1728-1732 (2005); or U.S. Pat. No. 5,599,675 or 5,750,341, each of which is incorporated herein by reference. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998); Fodor et al., *Science* 251(4995), 767-773 (1995); or PCT Pat. App. Publ. No. WO 1989/10977, each of which is incorporated herein by reference. In both sequencing-by-ligation and sequencing-by-hybridization procedures, target nucleic acids (or amplicons thereof) that are present at sites of an array are subjected to repeated cycles of oligonucleotide delivery and detection. Compositions, apparatus or methods set forth herein or in references cited herein can be readily adapted for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some sequencing embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zero-mode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), each of which is incorporated herein by reference.

Some sequencing embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies and Thermo Fisher subsidiary) or sequencing methods and systems described in US Pat app. Publ. Nos. 2009/0026082 A1; 2009/0127589 A1; 2010/0137143 A1; or US 2010/0282617 A1, each of which is incorporated herein by reference.

Nucleic acid hybridization techniques are also useful method for determining barcode sequences. In some cases combinatorial hybridization methods can be used such as those used for decoding of multiplex bead arrays (see e.g. U.S. Pat. No. 8,460,865, which is incorporated herein by reference). Such methods utilize labelled nucleic acid decoder probes that are complementary to at least a portion of a barcode sequence. A hybridization reaction can be carried out using decoder probes having known labels such that the location where the labels end up on the solid support identifies the nucleic acid probes according to rules of nucleic acid complementarity. In some cases, pools of many different probes with distinguishable labels are used, thereby allowing a multiplex decoding operation. The number of different barcodes determined in a decoding operation can exceed the number of labels used for the decoding operation. For example, decoding can be carried out in several stages where each stage constitutes hybridization with a different pool of decoder probes. The same decoder probes can be present in different pools but the label that is present on each decoder probe can differ from pool to pool (i.e. each decoder probe is in a different "state" when in different pools). Various combinations of these states and stages can be used to expand the number of barcodes that can be decoded well beyond the number of distinct labels available for decoding. Such combinatorial methods are set forth in further detail in U.S. Pat. No. 8,460,865 or Gunderson et al., *Genome Research* 14:870-877 (2004), each of which is incorporated herein by reference.

A method of the present disclosure can include a step of contacting a biological specimen with a solid support that has nucleic acid probes attached thereto. In some embodiments the nucleic acid probes are randomly located on the solid support. The identity and location of the nucleic acid probes may have been decoded prior to contacting the biological specimen with the solid support. Alternatively, the identity and location of the nucleic acid probes can be determined after contacting the solid support with the biological specimen.

In some embodiments the biological specimen is one or more cells. The cell(s) can be individual and free from any tissue or multicellular structure at the time contact is made with the solid support. For example, the cell(s) can be present in a fluid (e.g. when a plurality of different cells are present the fluid can be a fluidic mixture of the different cells) and the fluid can be contacted with the solid support to which the different probes are attached. Any of a variety of cells can be used including, for example, those from a prokaryote, archae or eukaryote. One or more cells used in a method, composition or apparatus of the present disclosure can be a single celled organisms or from a multicellular organism. Exemplary organisms from which one or more cell can be obtained include, but are not limited to a mammal, plant, algae, nematode, insect, fish, reptile, amphibian, fungi or Plasmodium falciparum. Exemplary species are set forth previously herein or known in the art.

Embodiments of the present disclosure can also use one or more subcellular components as a biological specimen. For example a fluidic mixture can include one or more nuclei, golgi apparatus, mitochondria, chloroplasts, membrane fractions, vesicles, endoplasmic reticulum, or other components known in the art. Other useful types of biological specimens are one or more viruses or a viroids.

It will be understood that a biological specimen can be a homogeneous culture or population of the above cells, subcellular components, viruses or viroids. Alternatively the biological specimen can be a non-homogenous collection of cells, subcellular components, viruses or viroids, for example, derived from several different organisms in a community or ecosystem. An exemplary community is the collection of bacteria present in the digestive system, lung or other organ of a multicellular organism such as a mammal.

One or more cells, subcellular components, viruses or viroids that are contacted with a solid support in a method set forth herein can be attached to the solid support. Attachment can be achieved using methods known in the art such as those exemplified herein with respect to attachment of nucleic acids to a solid support. In some embodiments, attachment is selective for specific types of cells, subcellular components, viruses or viroids. For example, the solid support can include antibodies or other receptors that are selective for epitopes or ligands present on one or a subset of different cells, subcellular components, viruses or viroids present in a fluidic mixture. In other embodiments, the attachment of cells, subcellular components, viruses or viroids can be mediated by non-selective moieties such as chemical moieties that are broadly reactive.

In particular embodiments, one or more cells, subcellular components, viruses or viroids that have been contacted with a solid support can be lysed to release target nucleic acids. Lysis can be carried out using methods known in the art such as those that employ one or more of chemical treatment, enzymatic treatment, electroporation, heat, hypotonic treatment, sonication or the like. Exemplary lysis techniques are set forth in Sambrook et al., *Molecular Cloning: A Laboratory Manual, Third Ed.*, Cold Spring Harbor Laboratory, New York (2001) and in Ansubel et al., *Current Protocols in Molecular Biology*, John Wiley and Sons, Baltimore, Md. (1999).

In some embodiments the biological specimen is a tissue section. The tissue can be derived from a multicellular organism such as those exemplified above in regard to cells. A tissue section can be contacted with a solid support, for example, by laying the tissue on the surface of the solid support. The tissue can be freshly excised from an organism or it may have been previously preserved for example by freezing, embedding in a material such as paraffin (e.g. formalin fixed paraffin embedded samples), formalin fixation, infiltration, dehydration or the like. Optionally, a tissue section can be attached to a solid support, for example, using techniques and compositions exemplified herein with regard to attaching nucleic acids, cells, viruses, beads or the like to a solid support. As a further option, a tissue can be permeabilized and the cells of the tissue lysed when the tissue is in contact with a solid support. Any of a variety of treatments can be used such as those set forth above in regard to lysing cells. Target nucleic acids that are released from a tissue that is permeabilized can be captured by nucleic acid probes on the surface.

A tissue can be prepared in any convenient or desired way for its use in a method, composition or apparatus herein. Fresh, frozen, fixed or unfixed tissues can be used. A tissue can be fixed or embedded using methods described herein or known in the art.

A tissue sample for use herein, can be fixed by deep freezing at temperature suitable to maintain or preserve the integrity of the tissue structure, e.g. less than −20° C. In another example, a tissue can be prepared using formalin-fixation and paraffin embedding (FFPE) methods which are known in the art. Other fixatives and/or embedding materials can be used as desired. A fixed or embedded tissue sample can be sectioned, i.e. thinly sliced, using known methods. For example, a tissue sample can be sectioned using a chilled microtome or cryostat, set at a temperature suitable to maintain both the structural integrity of the tissue sample and the chemical properties of the nucleic acids in the sample.

In some embodiments, a tissue sample will be treated to remove embedding material (e.g. to remove paraffin or formalin) from the sample prior to release, capture or modification of nucleic acids. This can be achieved by contacting the sample with an appropriate solvent (e.g. xylene and ethanol washes). Treatment can occur prior to contacting the tissue sample with a solid support set forth herein or the treatment can occur while the tissue sample is on the solid support. Exemplary methods for manipulating tissues for use with solid supports to which nucleic acids are attached are set forth in US Pat. App. Publ. No. 2014/0066318 A1, which is incorporated herein by reference.

The thickness of a tissue sample or other biological specimen that is contacted with a solid support in a method, composition or apparatus set forth herein can be any suitable thickness desired. In representative embodiments, the thickness will be at least 0.1 μm, 0.25 μm, 0.5 μm, 0.75 μm, 1 μm, 5 μm, 10 μm, 50 μm, 100 μm or thicker. Alternatively or additionally, the thickness of a biological specimen that is contacted with a solid support will be no more than 100 μm, 50 μm, 10 μm, 5 μm, 1 μm, 0.5 μm, 0.25 μm, 0.1 μm or thinner.

A particularly relevant source for a biological specimen is a human being. The specimen can be derived from an organ, including for example, an organ of the musculoskeletal system such as muscle, bone, tendon or ligament; an organ of the digestive system such as salivary gland, pharynx, esophagus, stomach, small intestine, large intestine, liver, gallbladder or pancreas; an organ of the respiratory system such as larynx, trachea, bronchi, lungs or diaphragm; an organ of the urinary system such as kidney, ureter, bladder or urethra; a reproductive organ such as ovary, fallopian tube, uterus, vagina, placenta, testicle, epididymis, vas deferens, seminal vesicle, prostate, penis or scrotum; an organ of the endocrine system such as pituitary gland, pineal gland, thyroid gland, parathyroid gland, or adrenal gland; an organ of the circulatory system such as heart, artery, vein or capillary; an organ of the lymphatic system such as lymphatic vessel, lymph node, bone marrow, thymus or spleen; an organ of the central nervous system such as brain, brainstem, cerebellum, spinal cord, cranial nerve, or spinal nerve; a sensory organ such as eye, ear, nose, or tongue; or an organ of the integument such as skin, subcutaneous tissue or mammary gland. In some embodiments, a biological specimen is obtained from a bodily fluid or excreta such as blood, lymph, tears, sweat, saliva, semen, vaginal secretion, ear wax, fecal matter or urine.

A specimen from a human can be considered (or suspected) healthy or diseased when used. In some cases, two specimens can be used: a first being considered diseased and a second being considered as healthy (e.g. for use as a healthy control). Any of a variety of conditions can be evaluated, including but not limited to, an autoimmune disease, cancer, cystic fibrosis, aneuploidy, pathogenic infection, psychological condition, hepatitis, diabetes, sexually transmitted disease, heart disease, stroke, cardiovascular disease, multiple sclerosis or muscular dystrophy. Particularly relevant conditions are genetic conditions or conditions associated with pathogens having identifiable genetic signatures.

As set forth above, a flow cell provides a convenient apparatus for use in a method set forth herein. For example, a flow cell is a convenient apparatus for housing a solid support that will be treated with multiple fluidic reagents such as the repeated fluidic deliveries used for some nucleic acid sequencing protocols or some nucleic acid hybridization protocols. In some embodiments, a biological specimen can be delivered to a solid support in a flow cell, for example, when a fluidic mixture of cells, subcellular components, viruses or viroids is delivered to the solid support. In some embodiments it may be preferable to open a flow cell to expose a solid support inside or to remove the solid support from the flow cell in order to allow convenient delivery of a biological specimen to the solid support. For example, opening the flow cell or removing the solid support can allow a user or robotic device to lay a tissue section on the solid support. The opening of a flow cell or removal of a solid support from a flow cell can be temporary. Thus, the flow cell can subsequently be closed or the solid support returned to the flow cell to proceed with one or more subsequent steps of a method set forth herein.

In some embodiments, a flow cell can have a construction that allows it to be opened or taken apart. For example the flow cell can be in a closed state while performing a sequencing reaction, for example to decode barcodes. Then the flow cell can be taken apart so that tissue can be placed on the flow cell surface. The flow cell can be held together by adhesive such that one or more surface can be removed to open it. For example, a flow cell can have a spacer with adhesive surfaces on the top or bottom (akin to single-sided or double-sided sticky tape) and this spacer can occur between two solid supports. One or both of the solid supports can be configured to attach nucleic acids and support a biological specimen as set forth herein. The spacer can have open regions (e.g. created by laser cutting of the spacer material) that create fluidic channels bound by the two solid supports and the spacer. Thus, one or both of the solid supports can be non-permanently adhered to the spacer to allow one or both of them to be removed to allow access to the surface when placing a tissue or other specimen thereon.

A nucleic acid probe used in a composition, apparatus or method set forth herein can include a target capture moiety. In particular embodiments, the target capture moiety is a target capture sequence. The target capture sequence is generally complementary to a target sequence such that target capture occurs by formation of a probe-target hybrid complex. A target capture sequence can be any of a variety of lengths including, for example, lengths exemplified above in the context of barcode sequences.

In multiplex embodiments, a plurality of different nucleic acid probes can include different target capture sequences that hybridize to different target nucleic acid sequences from a biological specimen. Different target capture sequences can be used to selectively bind to one or more desired target nucleic acids from a biological specimen. In some cases, the different nucleic acid probes can include a target capture sequence that is common to all or a subset of the probes on a solid support. For example, the nucleic acid probes on a solid support can have a poly A or poly T sequence. Such probes or amplicons thereof can hybridize to mRNA molecules, cDNA molecules or amplicons thereof that have poly A or poly T tails. Although the mRNA or cDNA species will have different target sequences, capture will be mediated by the common poly A or poly T sequence regions.

Any of a variety of target nucleic acids can be captured and analyzed in a method set forth herein including, but not limited to, messenger RNA (mRNA), copy DNA (cDNA), genomic DNA (gDNA), ribosomal RNA (rRNA) or transfer RNA (tRNA). Particular target sequences can be selected from databases and appropriate capture sequences designed using techniques and databases known in the art.

Other target capture moieties that are useful include, for example, the moieties set forth herein as useful for attaching nucleic acid probes to a solid support.

A method set forth herein can include a step of hybridizing nucleic acid probes, that are on a solid support, to target nucleic acids that are from portions of the biological specimen that are proximal to the probes. Generally, a target nucleic acid will diffuse from a region of the biological specimen to an area of the solid support that is in proximity with that region of the specimen. Here the target nucleic acid will interact with nucleic acid probes that are proximal to the region of the specimen from which the target nucleic acid was released. A target-probe hybrid complex can form where the target nucleic acid encounters a complementary target capture sequence on a nucleic acid probe. The location of the target-probe hybrid complex will generally correlate with the region of the biological specimen from where the target nucleic acid was derived. In multiplex embodiments, the solid support will include a plurality of nucleic acid probes, the biological specimen will release a plurality of target nucleic acids and a plurality of target-probe hybrids will be formed on the solid support. The sequences of the target nucleic acids and their locations on the support will provide spatial information about the nucleic acid content of the biological specimen. Although the example above is described in the context of target nucleic acids that are released from a biological specimen, it will be understood that the target nucleic acids need not be released. Rather, the target nucleic acids may remain in contact with the biological specimen, for example, when they are attached to an exposed surface of the biological specimen in a way that the target nucleic acids can also bind to appropriate nucleic acid probes on the solid support.

A method of the present disclosure can include a step of extending solid support-attached probes to which target nucleic acids are hybridized. In embodiments where the probes include barcode sequences, the resulting extended probes will include the barcode sequences and sequences from the target nucleic acids (albeit in complementary form). The extended probes are thus spatially tagged versions of the target nucleic acids from the biological specimen. The sequences of the extended probes identify what nucleic acids are in the biological specimen and where in the biological specimen the target nucleic acids are located. It will be understood that other sequence elements that are present in the nucleic acid probes can also be included in the extended probes. Such elements include, for example, primer binding sites, cleavage sites, other tag sequences (e.g. sample identification tags), capture sequences, recognition sites for nucleic acid binding proteins or nucleic acid enzymes, or the like.

Extension of probes can be carried out using methods exemplified herein or otherwise known in the art for amplification of nucleic acids or sequencing of nucleic acids. In particular embodiments one or more nucleotides can be added to the 3' end of a nucleic acid, for example, via polymerase catalysis (e.g. DNA polymerase, RNA polymerase or reverse transcriptase). Chemical or enzymatic methods can be used to add one or more nucleotide to the 3' or 5' end of a nucleic acid. One or more oligonucleotides can be added to the 3' or 5' end of a nucleic acid, for example, via chemical or enzymatic (e.g. ligase catalysis) methods. A nucleic acid can be extended in a template directed manner, whereby the product of extension is complementary to a template nucleic acid that is hybridized to the nucleic acid that is extended. In some embodiments, a DNA primer is extended by a reverse transcriptase using an RNA template, thereby producing a cDNA. Thus, an extended probe made in a method set forth herein can be a reverse transcribed DNA molecule. Exemplary methods for extending nucleic acids are set forth in US Pat. App. Publ. No. US 2005/0037393 A1 or U.S. Pat. No. 8,288,103 or 8,486,625, each of which is incorporated herein by reference.

All or part of a target nucleic acid that is hybridized to a nucleic acid probe can be copied by extension. For example, an extended probe can include at least, 1, 2, 5, 10, 25, 50, 100, 200, 500, 1000 or more nucleotides that are copied from a target nucleic acid. The length of the extension product can be controlled, for example, using reversibly terminated nucleotides in the extension reaction and running a limited number of extension cycles. The cycles can be run as exemplified for SBS techniques and the use of labeled nucleotides is not necessary. Accordingly, an extended probe produced in a method set forth herein can include no more than 1000, 500, 200, 100, 50, 25, 10, 5, 2 or 1 nucleotides that are copied from a target nucleic acid. Of course extended probes can be any length within or outside of the ranges set forth above.

Although the methods of the present disclosure are exemplified by an embodiment where probes that are hybridized to target nucleic acids are extended to copy at least a portion of the target nucleic acid, it will be understood that the probes can be modified in alternative ways. The probes that are hybridized to target nucleic acids can be subjected to a reaction that creates a target specific modification of the probe. A target specific modification will result only when the probe interacts with a target nucleic acid, for example, via complementary based hybridization. In many embodiments, the target specific modification will be specific to the sequence of the particular target nucleic acid that interacts with the probe. Examples of useful target specific modifications, include but are not limited to, insertion or addition of a sequence by ligation or transposition (see, for example, US Pat. App. Publ. No. 2010/0120098 A1, incorporated herein by reference), chemical modifications such as psoralen crosslinking or addition of a detectable tag moiety, modifications by nucleic acid enzymes, ligation of a hairpin linker, or other modifications set forth in the nucleic acid assays of US Pat. App. Publ. No. US 2005/0037393 A1 or U.S. Pat. No. 8,288,103 or 8,486,625, each of which is incorporated herein by reference.

It will be understood that probes used in a method, composition or apparatus set forth herein need not be nucleic acids. Other molecules can be used such as proteins, carbohydrates, small molecules, particles or the like. Probes can be a combination of a nucleic acid component (e.g. having a barcode, primer binding site, cleavage site and/or other sequence element set forth herein) and another moiety (e.g. a moiety that captures or modifies a target nucleic acid).

A method set forth herein can further include a step of acquiring an image of a biological specimen that is in contact with a solid support. The solid support can be in any of a variety of states set forth herein. For example, the solid support can include attached nucleic acid probes or clusters derived from attached nucleic acid probes. Alternatively, the solid support may not include nucleic acid probes, instead being in a state that precedes attachment of nucleic acid probes or in a state that follows removal of nucleic acid probes from the solid support. Accordingly, an image can be obtained at any of a variety of points in a method set forth herein.

An image can be obtained using detection devices known in the art. Examples include microscopes configured for light, bright field, dark field, phase contrast, fluorescence, reflection, interference, or confocal imaging. A biological specimen can be stained prior to imaging to provide contrast between different regions or cells. In some embodiments, more than one stain can be used to image different aspects of the specimen (e.g. different regions of a tissue, different cells, specific subcellular components or the like). In other embodiments, a biological specimen can be imaged without staining.

In particular embodiments, a fluorescence microscope (e.g. a confocal fluorescent microscope) can be used to detect a biological specimen that is fluorescent, for example, by virtue of a fluorescent label. Fluorescent specimens can also be imaged using a nucleic acid sequencing device having optics for fluorescent detection such as a Genome Analyzer®, MiSeq®, NextSeq® or HiSeq® platform device commercialized by Illumina, Inc. (San Diego, Calif.); or a SOLiD™ sequencing platform commercialized by Life Technologies (Carlsbad, Calif.). Other imaging optics that can be used include those that are found in the detection devices described in Bentley et al., *Nature* 456:53-59 (2008), PCT Publ. Nos. WO 91/06678, WO 04/018497 or WO 07/123744; U.S. Pat. No. 7,057,026, 7,329,492, 7,211,414, 7,315,019 or 7,405,281, and US Pat. App. Publ. No. 2008/0108082, each of which is incorporated herein by reference.

An image of a biological specimen can be obtained at a desired resolution, for example, to distinguish tissues, cells or subcellular components. Accordingly, the resolution can be sufficient to distinguish components of a biological specimen that are separated by at least 0.5 µm, 1 µm, 5 µm, 10 µm, 50 µm, 100 µm, 500 µm, 1 mm or more. Alternatively or additionally, the resolution can be set to distinguish components of a biological specimen that are separated by at least 1 mm, 500 µm, 100 µm, 50 µm, 10 µm, 5 µm, 1 µm, 0.5 µm or less.

A method set forth herein can include a step of correlating locations in an image of a biological specimen with barcode sequences of nucleic acid probes that are attached to a surface to which the biological specimen is, was or will be contacted. Accordingly, characteristics of the biological specimen that are identifiable in the image can be correlated with the nucleic acids that are found to be present in their proximity. Any of a variety of morphological characteristics can be used in such a correlation, including for example, cell shape, cell size, tissue shape, staining patterns, presence of particular proteins (e.g. as detected by immunohistochemical stains) or other characteristics that are routinely evaluated in pathology or research applications. Accordingly, the biological state of a tissue or its components as determined by visual observation can be correlated with molecular biological characteristics as determined by spatially resolved nucleic acid analysis.

A solid support upon which a biological specimen is imaged can include fiducial markers to facilitate determination of the orientation of the specimen or the image thereof in relation to probes that are attached to the solid support. Exemplary fiducials include, but are not limited to beads (with or without fluorescent moieties or moieties such as nucleic acids to which labeled probes can be bound), fluorescent molecules attached at known or determinable features, or structures that combine morphological shapes with fluorescent moieties. Exemplary fiducials are set forth in US Pat. App. Publ. No. 2002/0150909 A1 or U.S. patent application Ser. No. 14/530,299, each of which is incorporated herein by reference. One or more fiducials are preferably visible while obtaining an image of a biological specimen. Preferably, the solid support includes at least 2, 3, 4, 5, 10, 25, 50, 100 or more fiducial markers. The fiducials can be provided in a pattern, for example, along an outer edge of a solid support or perimeter of a location where a biological specimen resides. In a preferred embodiment, one or more fiducials are detected using the same imaging conditions used to visualize a biological specimen. However if desired separate images can be obtained (e.g. one image of the biological specimen and another image of the fiducials) and the images can be aligned to each other.

Optionally, a biological specimen, can be removed from a solid support after an image has been obtained and after target nucleic acids have been captured by nucleic acid probes on the solid support. Thus, a method of the present disclosure can include a step of washing a solid support to remove cells, tissue or other materials from a biological specimen. Removal of the specimen can be performed using any suitable technique and will be dependent on the tissue sample. In some cases, the solid support can be washed with water. The water can contain various additives, such as surfactants (e.g. detergents), enzymes (e.g. proteases and collagenases), cleavage reagents, or the like, to facilitate removal of the specimen. In some embodiments, the solid support is treated with a solution comprising a proteinase enzyme. Alternatively or additionally, the solution can include cellulase, hemicellulase or chitinase enzymes (e.g. if desiring to remove a tissue sample from a plant or fungal source). In some cases, the temperature of a wash solution will be at least 30° C., 35° C., 50° C., 60° C. or 90° C. Conditions can be selected for removal of a biological specimen while not denaturing hybrid complexes formed between target nucleic acids and solid support-attached nucleic acid probes.

A method of the present disclosure can further include a step of removing one or more extended probes from a solid support. In particular embodiments, the probes will have included a cleavage site such that the product of extending the probes will also include the cleavage site. Alternatively, a cleavage site can be introduced into a probe during a modification step. For example a cleavage site can be introduced into an extended probe during the extension step.

Exemplary cleavage sites include, but are not limited to, moieties that are susceptible to a chemical, enzymatic or physical process that results in bond breakage. For example, the location can be a nucleotide sequence that is recognized by an endonuclease. Suitable endonucleases and their recognition sequences are well known in the art and in many cases are even commercially available (e.g. from New England Biolabs, Beverley Mass.; ThermoFisher, Waltham, Mass. or Sigma Aldrich, St. Louis Mo.). A particularly useful endonuclease will break a bond in a nucleic acid strand at a site that is 3'-remote to its binding site in the nucleic acid, examples of which include Type II or Type IIs restriction endonucleases. In some embodiments an endonuclease will cut only one strand in a duplex nucleic acid (e.g. a nicking enzyme). Examples of endonucleases that cleave only one strand include Nt.BstNBI and Nt.Alwl.

In some embodiments, a cleavage site is an abasic site or a nucleotide that has a base that is susceptible to being removed to create an abasic site. Examples of nucleotides that are susceptible to being removed to form an abasic site include uracil and 8-oxo-guanine. Abasic sites can be created by hydrolysis of nucleotide residues using chemical or enzymatic reagents. Once formed, abasic sites may be cleaved (e.g. by treatment with an endonuclease or other single-stranded cleaving enzyme, exposure to heat or alkali), providing a means for site-specific cleavage of a nucleic acid. An abasic site may be created at a uracil nucleotide on one strand of a nucleic acid. The enzyme uracil DNA glycosylase (UDG) may be used to remove the uracil base, generating an abasic site on the strand. The nucleic acid strand that has the abasic site may then be cleaved at the abasic site by treatment with endonuclease (e.g. EndoIV endonuclease, AP lyase, FPG glycosylase/AP lyase, EndoVIII glycosylase/AP lyase), heat or alkali. In a particular embodiment, the USER™ reagent available from New England Biolabs is used for the creation of a single nucleotide gap at a uracil base in a nucleic acid.

Abasic sites may also be generated at non-natural/modified deoxyribonucleotides other than uracil and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease (e.g. EndoIV or AP lyase).

Other examples of cleavage sites and methods that can be used to cleave nucleic acids are set forth, for example, in U.S. Pat. No. 7,960,120, which is incorporated herein by reference.

Modified nucleic acid probes (e.g. extended nucleic acid probes) that are released from a solid support can be pooled to form a fluidic mixture. The mixture can include, for example, at least 10, 100, $1 \times 10^3$, $1 \times 10^4$, $1 \times 10^5$, $1 \times 10^6$, $1 \times 10^7$, $1 \times 10^8$, $1 \times 10^9$ or more different modified probes. Alternatively or additionally, a fluidic mixture can include at most $1 \times 10^9$, $1 \times 10^8$, $1 \times 10^7$, $1 \times 10^6$, $1 \times 10^5$, $1 \times 10^4$, $1 \times 10^3$, 100, 10 or fewer different modified probes. The fluidic mixture can be manipulated to allow detection of the modified nucleic acid probes. For example, the modified nucleic acid probes can be separated spatially on a second solid support (i.e. different from the solid support from which the nucleic acid probes were released after having been contacted with a biological specimen and modified), or the probes can be separated temporally in a fluid stream.

Modified nucleic acid probes (e.g. extended nucleic acid probes) can be separated on a solid support in a capture or detection method commonly employed for microarray-based techniques or nucleic acid sequencing techniques such as those set forth previously herein. For example, modified probes can be attached to a microarray by hybridization to complementary nucleic acids. The modified probes can be attached to beads or to a flow cell surface and optionally amplified as is carried out in many nucleic acid sequencing platforms. Modified probes can be separated in a fluid stream using a microfluidic device, droplet manipulation device, or flow cytometer. Typically, detection is carried out on these separation devices, but detection is not necessary in all embodiments.

A particularly useful droplet manipulation device is a droplet actuator as described for example in U.S. Pat. Nos. 8,637,242, 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S. Pat. No. 6,773,566, entitled "Electrostatic Actuators for Microfluidics and Methods for Using Same," issued on Aug. 10, 2004; Shenderov, U.S. Pat. No. 25 6,565,727, entitled "Actuators for Microfluidics Without Moving Parts," issued on May 20, 2003; Kim et al., U.S. Patent Pub. No. 20030205632, entitled "Electrowetting driven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Microfluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 15 20060039823, entitled "Chemical Analysis Apparatus," published on Feb. 23, 2006; Wu, U.S. Patent Pub. No. 20110048951, entitled "Digital Microfluidics Based Apparatus for Heat-exchanging Chemical Processes," published on Mar. 3, 2011; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," Lab Chip, 10:832-836 (2010), each of which is incorporated herein by reference.

Modified probes (e.g. extended nucleic acid probes) can be detected, for example, following separation from a fluidic mixture using methods set forth above or known in the art. In particular embodiments, modified probes that are separated on a second solid support (i.e. a solid support that is different from the first solid support where contact was made between probes and biological specimen) can be detected using microarray-based techniques or nucleic acid sequencing techniques such as those set forth previously herein. Probes that are separated in a fluid stream can be detected using optical, electrical or other detectors that are outfitted in known microfluidic devices, droplet manipulation devices, or flow cytometers. A detection method can be used to determine target nucleic acid sequences, barcode sequences or other sequence regions of extended probes.

Several embodiments have been exemplified with regard to removing modified probes from the solid support where the probes were produced. However, it will be understood that probes on a solid support can be contacted with a biological specimen, modified on the solid support in the presence of target nucleic acids from the specimen and then the modified probes can be detected on the solid support. In such an embodiment, the biological specimen can be removed from the solid support prior to the detection step.

In particular embodiments the present disclosure provides a method for spatially tagging nucleic acids of a biological specimen that includes the steps of (a) providing a plurality of nucleic acid primers attached to a solid support, wherein the nucleic acid primers in the plurality include a universal primer sequence that is common to the nucleic acid primers in the plurality; (b) binding a population of nucleic acid probes to the plurality of nucleic acid primers, wherein the nucleic acid probes include a universal primer binding sequence that hybridizes to the universal primer sequence, a target capture sequence and a barcode sequence that differs from barcode sequences of other nucleic acid probes in the population, thereby attaching the different nucleic acid probes at randomly located positions on the solid support; (c) amplifying the different nucleic acid probes by extension of the nucleic acid primers, thereby producing nucleic acid clusters having copies of the barcode sequence and target capture sequence at the randomly located positions on the solid support; (d) performing a sequencing reaction to determine the barcode sequences at the randomly located positions on the solid support; (e) contacting a biological specimen with the nucleic acid clusters on the solid support; (f) hybridizing the target capture sequences of the clusters to target nucleic acids from portions of the biological specimen that are proximal to the clusters; and (g) extending the target capture sequences to produce extended probes that include sequences from the target nucleic acids and the copies of the barcode sequences, thereby tagging the nucleic acids of the biological specimen.

As exemplified previously herein, a plurality of nucleic acid primers can be attached to a solid support, wherein the nucleic acid primers in the plurality include a universal primer sequence that is common to the nucleic acid primers in the plurality. In this embodiment, a second plurality of nucleic acid primers can be attached to the solid support, and the nucleic acid primers in the second plurality can have a second universal primer sequence that is common to the nucleic acid primers in the second plurality. In this embodiment, a plurality of different nucleic acid probes that is contacted with the support can include a universal primer binding sequence that hybridizes to the universal primer on the solid support, as set forth above, and the different nucleic acid probes can also include a second universal primer binding sequence that hybridizes to the second universal primer sequence. This configuration of universal primers and universal primer binding sites can be particularly useful for amplifying the different nucleic acid probes via bridge amplification, wherein the nucleic acid primers in the first and second plurality are extended.

Typically, when a nucleic acid probe contains first and second universal primer binding sites, they will be located at the ends of the probe. In some embodiments it may be desirable to remove at least one of the primer binding sites from the nucleic acid probe or from amplicons produced from the probe. Accordingly, the nucleic acid probes can optionally include a cleavage site between the target capture sequence and one of the universal primer binding sequence. In this case, a cleavage reaction can be performed to separate the universal primer binding site from the target capture sequence. Generally, the portion of the probe (or its amplicons) that contains the target capture sequence will be attached to the solid support resulting in removal of the primer binding site from the solid support and retention of the target capture sequence. Thus, the cleaved probe can be used for hybridizing target nucleic acids and the cleaved probe can be extended using method set forth previously herein.

In some embodiments, a nucleic acid probe will include two different cleavage sites. A first cleavage site will be located between a first primer binding site and one or more other sequence elements of the probe. A second cleavage site can be located between a second primer binding site and the one or more other sequence elements of the probe. The cleavage sites can be reactive to different cleavage reactions such that each one can be selectively cleaved without necessarily cleaving the other. Accordingly, the first cleavage site can be cleaved prior to modifying the probe (for example, prior to producing an extended probe), thereby separating the first primer binding site from the one or more other sequence elements that remain attached to a solid support. The second cleavage site can be cleaved after modifying the probe (for example, after producing the extended probe), thereby releasing the modified probe for subsequent detection.

Alternatively, a nucleic acid probe can include the first cleavage site and a primer that is used to capture or amplify the nucleic acid probe can include the second cleavage site. In this configuration, the first cleavage site can be located between a first primer binding site and one or more other sequence elements of the probe such that cleavage separates the first primer binding site from one or more other sequence elements of the probe that remain attached to a solid support. Again, this first cleavage step will typically be carried out prior to modifying the probe (for example, prior to producing an extended probe). A second cleavage step can be carried out to cleave the second cleavage site after modifying the probe (for example, after producing the extended probe), thereby releasing the modified probe for subsequent detection.

The two embodiments above exemplify a cleavage site located between a point of attachment of a nucleic acid probe (or modified nucleic acid probe) and one or more sequences of the probe (or modified probe) that contain information such as a spatial barcode or target sequence. Thus, this cleavage site is useful for release of modified probes (e.g. extended probes) to detect the sequence information and determine what sequences are present in a biological specimen and where the sequences are present in the specimen.

In some embodiments, one or more probes that are contacted with a solid support in a method set forth herein can include a sequencing primer binding site. Accordingly, a modified probe (e.g. extended probe) can be detected in a sequencing technique that includes a step of hybridizing a sequencing primer to the sequencing primer binding site. The sequencing primer binding site can be located in the probe such that cleavage of a modified version of the probe (e.g. an extended probe) will yield a released probe that includes the sequencing primer binding site. The sequencing primer binding site can be a universal sequencing primer binding site such that a plurality of different probes (e.g. having different barcode and/or target sequences) will have the same sequencing primer binding site.

This disclosure further provides a method for spatially tagging nucleic acids of a biological specimen, the method including steps of (a) providing an array of beads on a solid support, wherein different nucleic acid probes are attached to different beads in the array, wherein the different nucleic acid probes each include a barcode sequence, wherein each bead includes a different barcode sequence from other beads on the solid support, and wherein each of the different nucleic acid probes includes a target capture sequence; (b) performing a decoder probe hybridization reaction on the solid support to determine the barcode sequences at the randomly located probes on the solid support; (c) contacting a biological specimen with the array of beads; (d) hybridizing the different nucleic acid probes to target nucleic acids from portions of the biological specimen that are proximal to the beads; and (e) extending the different nucleic acid probes to produce extended probes that include sequences from the target nucleic acids and the barcode sequences, thereby tagging the nucleic acids of the biological specimen.

It will be understood that manipulations of solid supports or of nucleic acids attached to solid supports can be carried out using beads as solid supports. The beads can be attached to a surface (e.g. an array of wells as in a BeadArray™ from Illumina) before or after such manipulations are carried out. For example, nucleic acid probes can be captured on beads before or after the beads are distributed on an array, nucleic acid probes can be amplified to create amplicons on beads before or after the beads are distributed on an array etc.

Example I

Spatially Tagging mRNA from a Tissue Sample Using Illumina Flow Cells

A method for generating barcoded oligo-dT containing clusters, then revealing the barcoded oligo-dT with a restriction enzyme digest followed by sequencing is described in FIG. 1. A library of fragments containing a single stranded, barcoded oligo-dA, P5', P7, SBS3 sequencing primer binding site and a BspH1 restriction enzyme site (shown in the top panel of FIG. 1) were prepared by oligo synthesis (Integrated DNA Technologies). The barcodes were 27mers and were randomly generated during synthesis. The binding site for the SBS3 sequencing primer was included for decoding of the barcode by sequencing. An oligo-dA stretch was included to generate an oligo dT site upon clustering and linearization. Bridge amplification and clustering were performed according to standard cluster chemistry (Illumina TruSeq PE Cluster Kit v3 cBot P/N: 15037931) on an Illumina GA flow cell using manufacture's recommended protocol.

Following bridge amplification and clustering the clusters were linearized by cleavage of 8-oxo-G in P7 primer using Formamidopyrimidine DNA glycosylase (Fpg) enzyme provided in the TruSeq PE Cluster kit. This was followed by restriction enzyme digest with 200 Units/mL BspH1 (NEB Cat # R0517L at 37° C. for 15 min to remove P7' from the P5 adapter anchored strand of the cluster to unveil the oligo-dT stretch for subsequent extension in the presence of an mRNA. Enzyme concentrations in the range of 100-400 U/mL have been tested for 15 or 30 min. The de-coding of the barcode was initiated by the SBS3 sequencing primer.

As shown in the bottom panel of FIG. 1, oligo-dT sequences in the cluster were used to capture poly A+ RNA after decoding of the barcode. Barcoded cDNA was produced by extension of the oligo-dT strand of the cluster using TruSeq RNA Sample Prep Kit (Illumina P/N: 15012997) and MMLV Reverse Transcriptase 1st-Strand cDNA Synthesis Kit (Epicentre P/N: MM070150) according to the manufacturer's recommended conditions. The captured RNA was used as a template. Barcoded cDNA was released from the P5 sequence of the flow cell using Illumina's Uracil Specific Excision reagents (USER) (Illumina's TruSeq PE cluster kit) liberating a barcoded cDNA library that was used for sequencing on a second Illumina flow cell.

Figure 2:
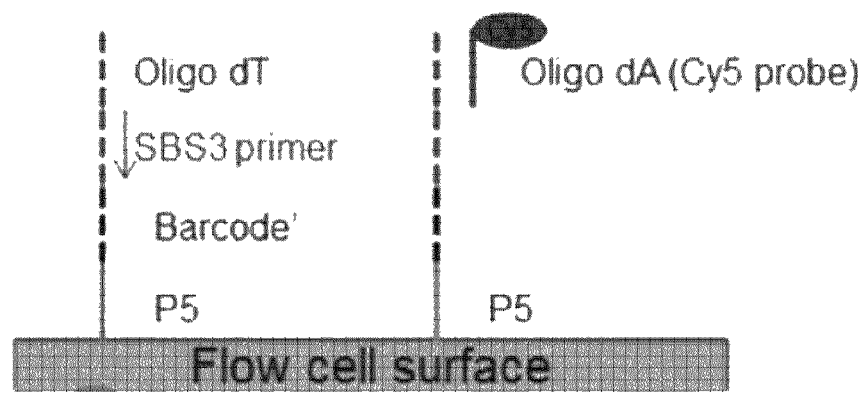
FIG. 2 shows data indicating the availability of oligo dT capture sequences on probes after bridge amplification of the probes and restriction enzyme digest with BspH1 to remove one of the primer binding sites used for bridge amplification.
Figure 2:
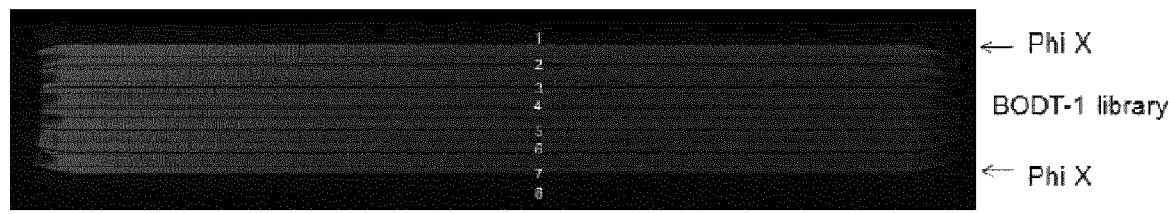
Figure 2:
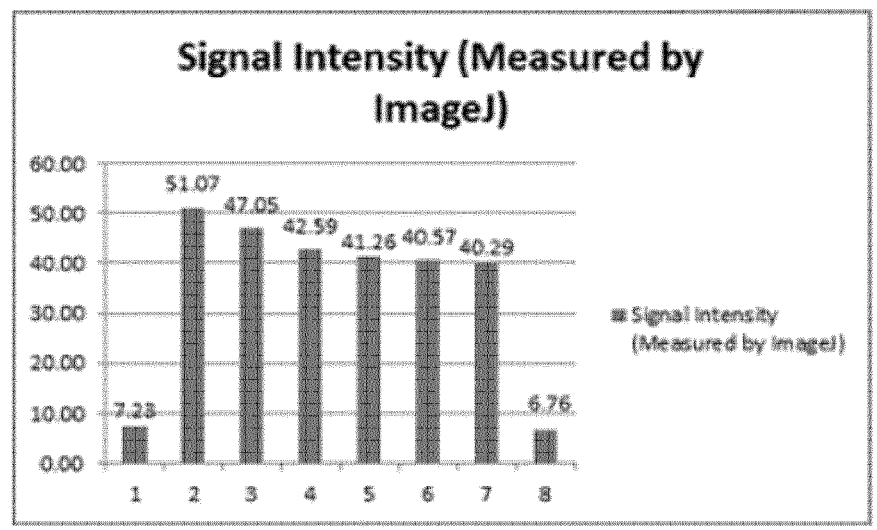

The availability of oligo dT capture sequence after the restriction enzyme digest with BspH1 was confirmed by hybridizing the linearized clusters with a Cy5 labeled poly A (24mer) as diagrammed in panel A of FIG. 2. Briefly, after the restriction enzyme digestion, the clusters were treated with 0.1N NaOH and washed with HT2 low salt buffer to remove the second strand on the flow cell. Then, 500 nM of Cy5 oligo-dA (24mer) was flowed over the linearized and denatured clusters at 30 µl/min rate and incubated at 40° C. for 5 min and then imaged. Hybridization of Cy5 labeled poly A to the oligo dT was detected in lanes 2-7 of the GA flow cell where the oligo dT containing BODT-1 libraries were present (see the image of the flow cell shown in FIG. 2, Panel B). As evident from the flow cell image (Panel B), and the bargraph (Panel C), the control PhiX libraries (lanes 1 and 8 of the flow cell) were shown to have very low fluorescence in the Cy5 signal. These results demonstrated that an oligo-dT site can be created in the cluster that upon linearization can bind specifically to Cy5 poly A (24mer).

Figure 4:
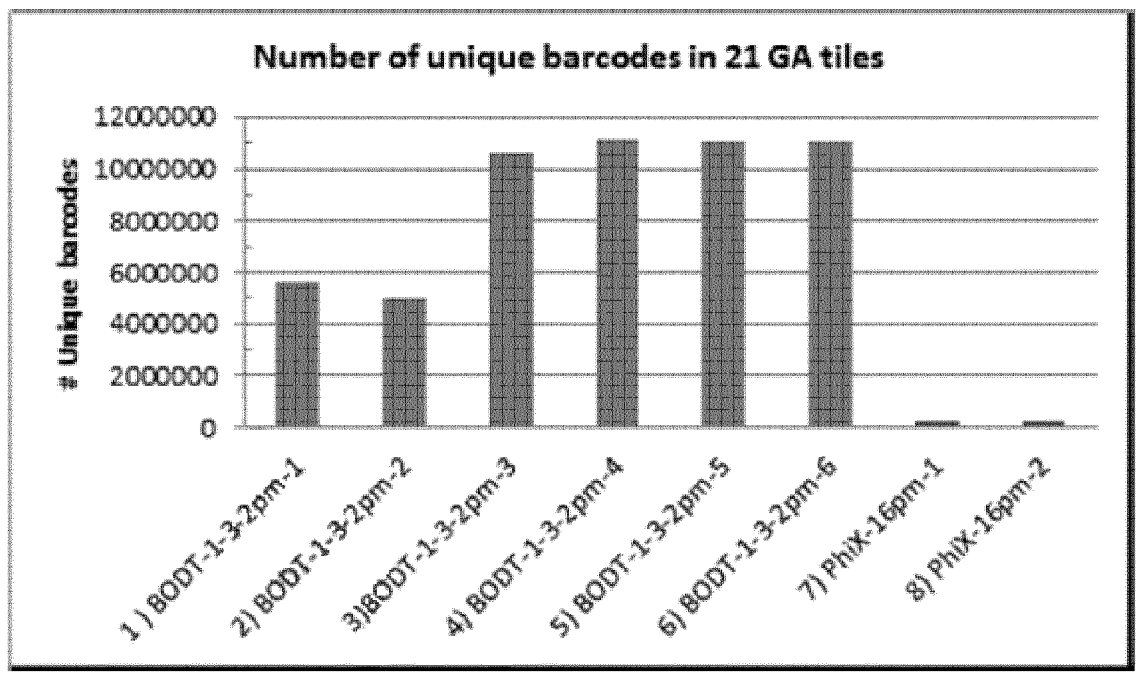
FIG. 4 the number of unique barcodes determined in 21 tiles of the flow cell described in Example 1 and shown in FIG. 2.

The sequencing metrics of the flow cell described above with 3.2 pM of BODT-1 library is given in the table shown in FIG. 3. Millions of reads were detected in 21 tiles from GA sequencing. Following sequencing, the number of unique barcodes were determined as plotted in FIG. 4. This was done by assuming that every passing filter (PF) read was a barcode and determining the number of unique reads (barcodes) in each lane. Between 5 and 11 million unique barcoded clusters were detected after sequencing tiles compared to the PhiX control libraries. These results demonstrated that sequence decoding of a library of barcoded oligo-dT sequences is feasible and generates millions of unique barcodes.

Example II

Cell Adhesion on Illumina Flow Cells

Single cells were captured on a patterned flow cell (HiSeq X10 flow cell, Illumina). All reagent flow steps were performed using a peristaltic pump or the cBOT cluster generation instrument (Illumina). Briefly, nuclease free water was flowed on all lanes of the patterned flow cell followed by 30-70K Poly D Lysine Solution (100 µg/ml and 20 µg/ml) at a flow rate of 100 µl/min for 8 min. Heat inactivated Fetal Bovine Serum (Life Technologies #10082-139) was also tested as an adhesive. The adhesives were incubated on the flow cell lanes for 1 hr, followed by a 1× PBS+0.5% Pluronic F-68 (Life Technologies #24040-032) wash. Next, the cells were adhered to the coated flow cells by flowing 5 to 50 cells/µl or approximately 100-1000 cells per lane at a rate of 100 µl/min, followed by an incubation step for 60 min to bind the cells. The flow cell was washed with 1× PBS/ 0.5% pluronic at a rate of 75 µl/min. If cells were fixed on the flow cell, 1% Paraformaldehyde (PFA) was flowed on the flow cell after flowing the cells as described above and incubated for 15 min followed by the 1× PBS/0.5% pluronic was step. The flow cell was removed and the number of cells per lane counted using a microscope.

Figure 5:
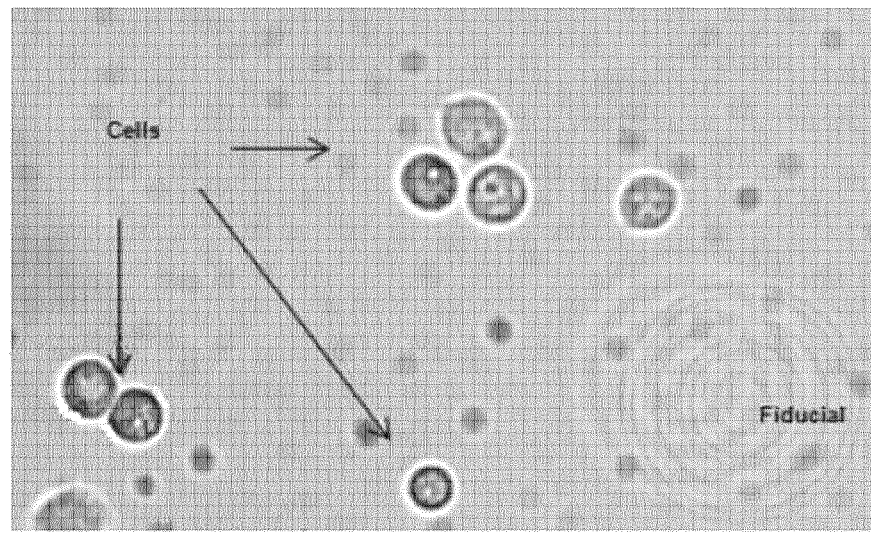
FIG. 5 shows an image of cells captured on a patterned flow cell (Panel A) and cell count data (Panel B).
Figure 5:
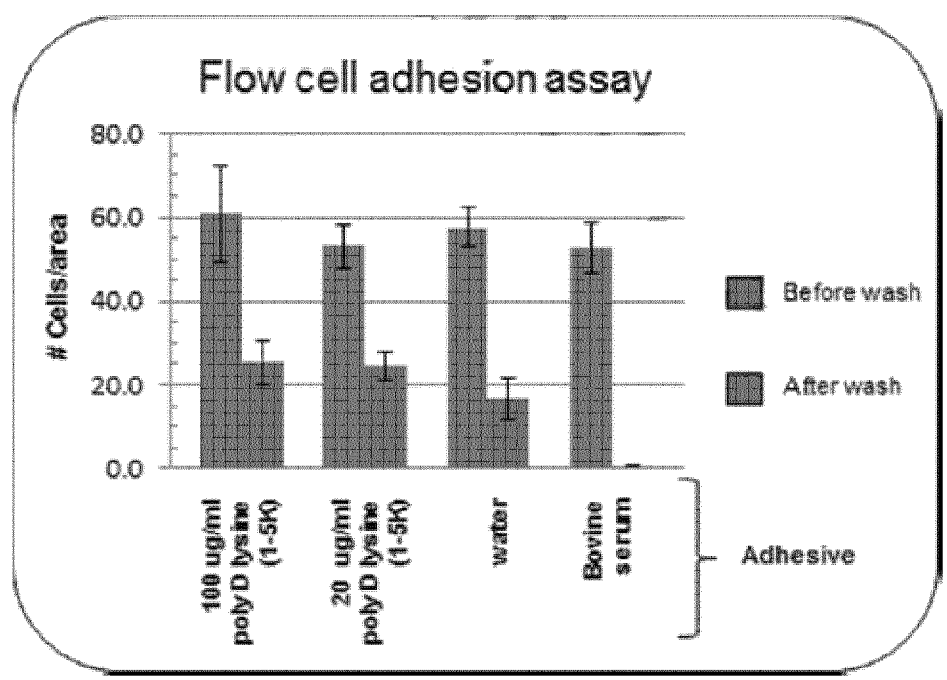
Figure 6:
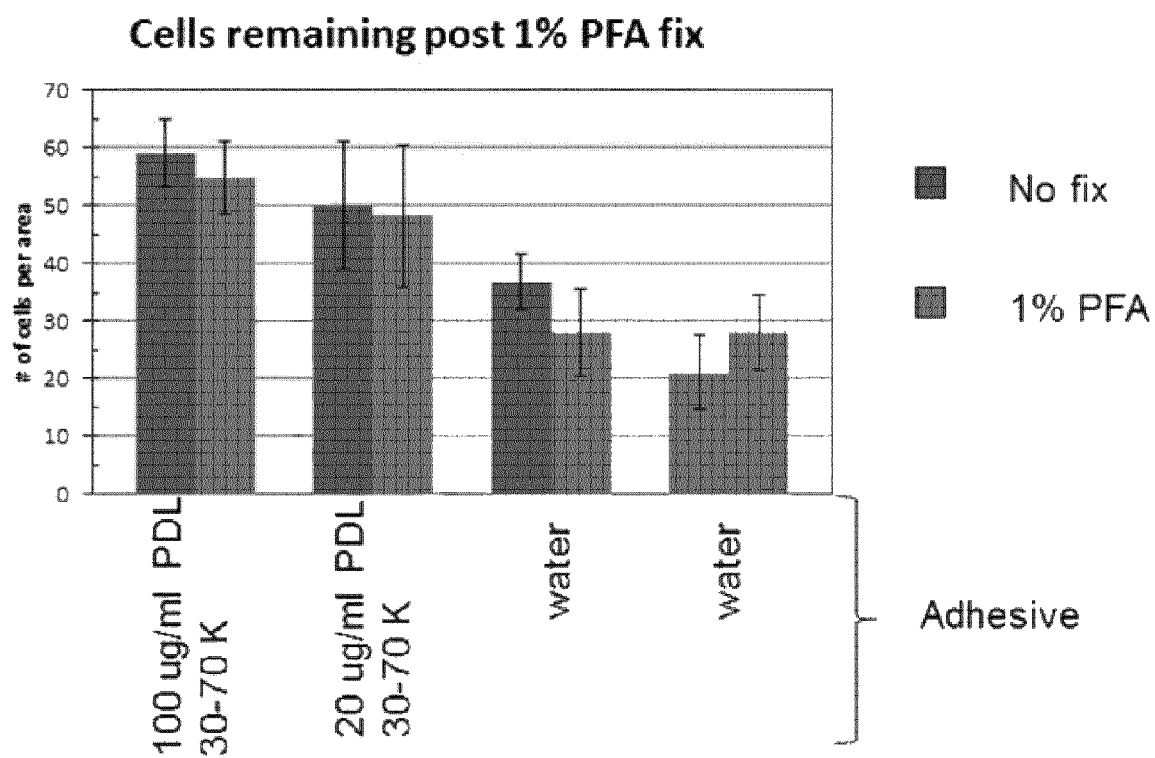
FIG. 6 shows cells that remain adhered to a flow cell in different conditions.

FIG. 5, Panel A shows an image of cells captured on the patterned flow cell. The cell count data shown in FIG. 5, Panel B confirmed that the poly D Lysine coated flow cells aided cell adherence compared to the BSA coated or no adhesive treated control. As shown in FIG. 6, the adhered cells can be successfully fixed with 1% PFA.

Example III

Spatially Localized Capture of Target mRNA by Probes Attached to a Gel Surface

This example describes creation of a lawn of poly T probes on a gel coated slide, placement of tissue slices on top of a lawn of poly T probes, release of RNA from the tissue sections, capture of the released mRNA by the poly T probes, reverse transcription to Cy 3 label the poly T probes, removal of the tissue and imaging of the slide.

Figure 7:
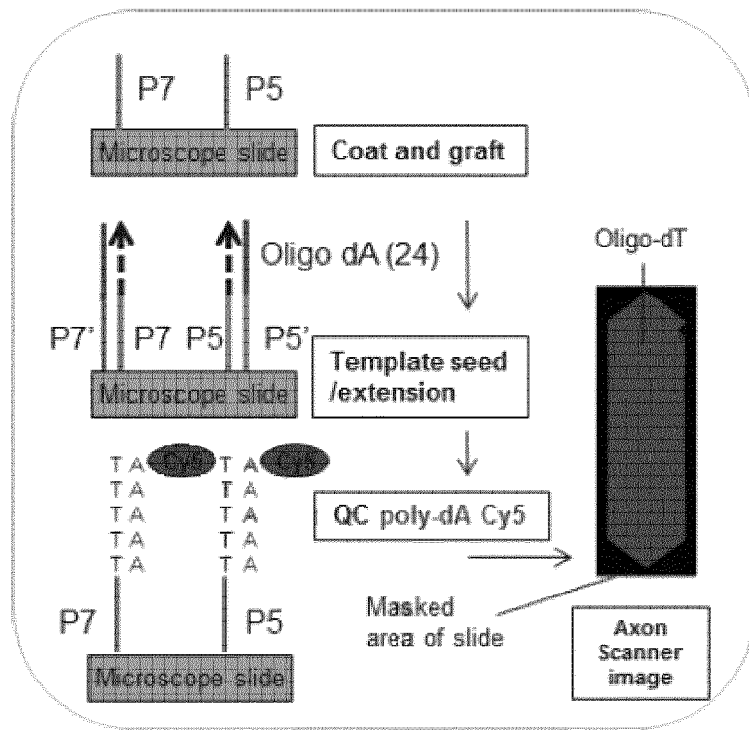
FIG. 7 shows a diagrammatic representation of steps and reagents used to create probes attached to a gel (Panel A), a diagrammatic representation of steps and reagents used to capture target nucleic acids using the gel-attached probes and fluorescently label the probes (Panel B), and an image created by the fluorescently labeled target nucleic acids following capture by the probes and removal of the tissue from the gel.
Figure 7:
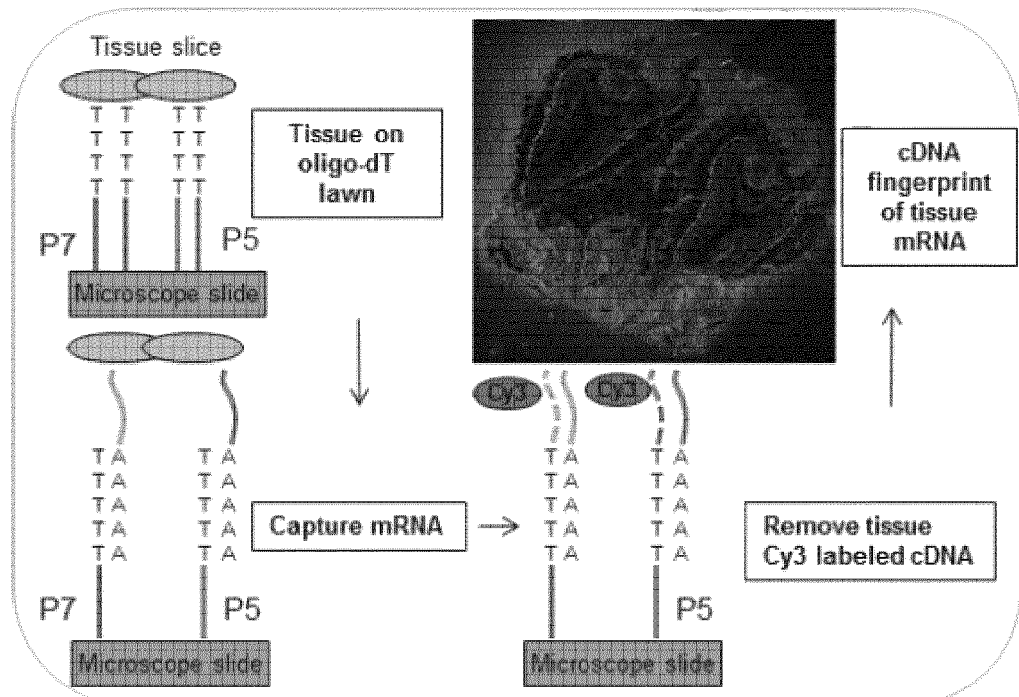

FIG. 7, Panel A shows a diagrammatic representation of steps and reagents used to create probes attached to a gel. Briefly, a microscope slide was coated with silane free acrylamide (SFA), P5 and P7 primers were attached (see US Pat. App. Pub. No. 2011/0059865 A1, which is incorporated herein by reference), probes having a poly A sequence and either a P5 or P7 complementary sequence were hybridized to the P5 and P7 primers, respectively, and the P5 and P7 primers were extended to produce poly T sequence extensions. A quality control step was performed by hybridizing Cy5 labeled polyA oligonucleotides to the extended primers and imaging the surface using an Axon Imager.

As shown in Panel B of FIG. 7, a tissue section was placed on the gel having the polyT extended primers. The tissue was treated to release mRNA and poly A tails of the released mRNA were hybridized to poly T sequences of the extended primers. The poly T sequences were extended using the captured mRNAs as templates and the extended primers were selectively labeled with Cy3. The tissue was removed from the gel and the surface was imaged to detect Cy3 fluorescence.

As shown in the image of FIG. 7, areas of the gel that were proximal to areas of the tissue that released mRNA species appeared fluorescent while areas that did not release mRNA appeared dark in the image. Thus, the captured mRNA created a fingerprint-like image of the tissue.

Example IV

Spatially Localized Capture of Target mRNA by Probes Attached to a BeadArray™ Surface This example describes placement of tissue slices on top of a BeadArray™ having poly T probes, release of RNA from the tissue sections, capture of the released mRNA by the poly T probes, reverse transcription to Cy5 label the poly T probes, removal of the tissue and imaging of the BeadArray™.

Figure 8:
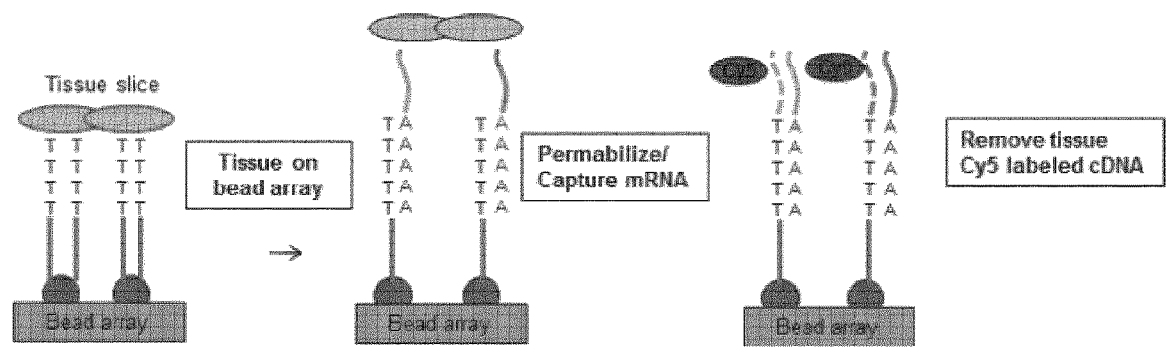
FIG. 8 shows a diagrammatic representation of steps and reagents used to capture target nucleic acids using BeadArray™-attached probes and fluorescently label the probes (Panel A), and an image created by the fluorescently labeled target nucleic acids following capture by the probes and removal of the tissue from the BeadArray™.
Figure 8:
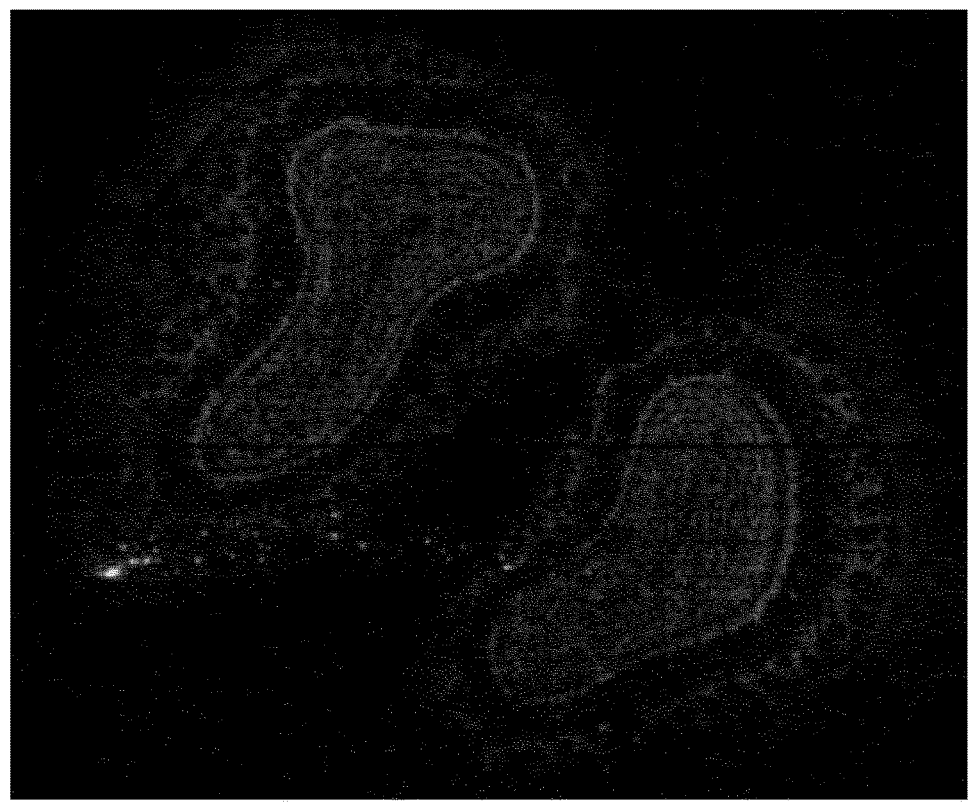

As shown in Panel A of FIG. 8, a mouse olfactory tissue section was placed on a BeadArray™ having polyT probes. The tissue was treated to release mRNA and poly A tails of the released mRNA were hybridized to poly T sequences of the probes. The poly T sequences were extended using the captured mRNAs as templates and the extended primers were selectively labeled with Cy5. The tissue was removed from the BeadArray™ and the BeadArray™ was imaged to detect Cy5 fluorescence.

As shown in Panel B of FIG. 7, areas of the BeadArray™ that were proximal to areas of the tissue that released mRNA species appeared fluorescent while areas that did not release mRNA appeared dark in the image. Thus, the captured mRNA created a fingerprint-like image of the tissue.

Throughout this application various publications, patents or patent applications have been referenced. The disclosure of these publications in their entireties are hereby incorporated by reference in this application.

The term "comprising" is intended herein to be open-ended, including not only the recited elements, but further encompassing any additional elements.

A number of embodiments have been described. Nevertheless, it will be understood that various modifications may be made. Accordingly, other embodiments are within the scope of the following claims.

The invention claimed is:

1. A method for spatially tagging target nucleic acids of a biological specimen, comprising:
   (a) providing a plurality of nucleic acid primers attached to a solid support, wherein the nucleic acid primers in the plurality comprise a universal primer sequence that is common to the nucleic acid primers in the plurality;
   (b) randomly distributing and binding a population of nucleic acid probes to the plurality of nucleic acid primers, wherein the nucleic acid probes comprise a universal primer binding sequence that hybridizes to the universal primer sequence, a target capture sequence, and a spatial tag sequence that differs from spatial tag sequences of other nucleic acid probes in the population, thereby attaching the nucleic acid probes at randomly located positions on the solid support;
   (c) amplifying the nucleic acid probes by extension of the nucleic acid primers, thereby producing nucleic acid clusters having copies of the spatial tag sequence and target capture sequence at the randomly located positions on the solid support;
   (d) performing a sequencing reaction to determine the spatial tag sequences at the randomly located positions on the solid support, thereby determining the position of each of the spatial tag sequences on the solid support;
   (e) contacting a biological specimen with the nucleic acid clusters on the solid support;
   (f) hybridizing the target capture sequences of the nucleic acid clusters to target nucleic acids from portions of the biological specimen that are proximal to the nucleic acid clusters; and
   (g) extending the target capture sequences to produce extended probes that comprise sequences of the target nucleic acids, or portions thereof, and the copies of the spatial tag sequences, thereby spatially tagging the target nucleic acids of the biological specimen.

2. The method of claim 1, wherein the nucleic acid clusters on the solid support have an average pitch of less than 10 μm and/or an average area of less than 100 μm².

3. The method of claim 1, wherein the method further comprises attaching the plurality of nucleic acid primers to the solid support, wherein the solid support comprises a pattern of discrete features.

4. The method of claim 1, wherein the solid support comprises a gel coating, wherein the plurality of nucleic acid primers is attached to the gel coating.

5. The method of claim 4, wherein in step (c), a second plurality of nucleic acid primers is further attached to the gel coating, the nucleic acid primers in the second plurality comprise a second universal primer sequence that is common to the nucleic acid primers in the second plurality, the nucleic acid probes comprise a second universal primer binding sequence that hybridizes to the second universal primer sequence, and the amplifying comprises bridge amplification.

6. The method of claim 1, wherein different nucleic acid probes comprise different target capture sequences that hybridize to different target nucleic acids from the biological specimen.

7. The method of claim 1, wherein different nucleic acid probes comprise a common target capture sequence, and the common target capture sequence comprises a poly T or poly A sequence.

8. The method of claim 1, further comprising a step of acquiring an image of the biological specimen in contact with the solid support, and a step of correlating the determined spatial tag sequences at the randomly located positions on the solid support with locations in the image of the biological specimen.

9. The method of claim 1, further comprising removing the extended probes from the solid support and determining the sequences of the target nucleic acids or portions thereof, and the spatial tag sequences for the extended probes that have been removed from the solid support.

10. The method of claim 9, wherein determining the sequences of the target nucleic acids, or portions thereof, and the spatial tag sequences for the extended probes that have been removed from the solid support comprises sequencing-by-synthesis.

11. The method of claim 1, further comprising removing the extended probes from the solid support and attaching the extended probes that have been removed from the solid support to a second solid support.

12. The method of claim 1, wherein the solid support is located in or on a flow cell during step (d), and the solid support is removed from the flow cell during step (e) or the flow cell is opened to expose the solid support during step (e).

13. The method of claim 1, wherein the biological specimen that is contacted with the solid support is a mixture of cells, and step (e) further comprises attaching the cells to the solid support and/or lysing the cells to release the target nucleic acids from the cells.

14. The method of claim 1, wherein the biological specimen that is contacted with the solid support is a tissue, and step (e) further comprises attaching the tissue to the solid support and/or permeabilizing the tissue to release the target nucleic acids from the tissue.

15. The method of claim 1, wherein the target nucleic acids are selected from the group consisting of mRNA, gDNA, rRNA, and tRNA.

16. The method of claim 1, wherein a second plurality of nucleic acid primers is attached to the solid support, wherein the nucleic acid primers in the second plurality comprise a second universal primer sequence that is common to the nucleic acid primers in the second plurality.

17. The method of claim 16, wherein the nucleic acid probes comprise a second universal primer binding sequence that hybridizes to the second universal primer sequence.

18. The method of claim 17, wherein the amplifying of the nucleic acid probes comprises bridge amplification wherein the nucleic acid primers in the first and second plurality are extended.

19. The method of claim 1, further comprising, after step (c), digesting the nucleic acid clusters with a restriction enzyme, thereby revealing the target capture sequences.

20. A method for spatially tagging target nucleic acids of a biological specimen, comprising:
(a) providing a plurality of nucleic acid primers attached to a solid support, wherein the nucleic acid primers in the plurality comprise a universal primer sequence that is common to the nucleic acid primers in the plurality;
(b) randomly distributing and binding a population of nucleic acid probes to the plurality of nucleic acid primers, wherein the nucleic acid probes comprise a universal primer binding sequence that hybridizes to the universal primer sequence, a target capture sequence, and a spatial tag sequence that differs from spatial tag sequences of other nucleic acid probes in the population, thereby attaching the nucleic acid probes at randomly located positions on the solid support;
(c) amplifying the nucleic acid probes by extension of the nucleic acid primers, thereby producing nucleic acid clusters having copies of the spatial tag sequence and target capture sequence at the randomly located positions on the solid support;
(d) performing a nucleic acid detection reaction to determine the spatial tag sequences at the randomly located positions on the solid support, thereby determining the position of each of the spatial tag sequences on the solid support;
(e) contacting a biological specimen with the nucleic acid clusters on the solid support;
(f) hybridizing the target capture sequences of the nucleic acid clusters to target nucleic acids from portions of the biological specimen that are proximal to the nucleic acid clusters; and
(g) extending the target capture sequences to produce extended probes that comprise sequences of the target nucleic acids, or portions thereof, and the copies of the spatial tag sequences, thereby spatially tagging the target nucleic acids of the biological specimen.

21. The method of claim 20, wherein the nucleic acid detection reaction comprises a decoder probe hybridization reaction.

22. The method of claim 20, wherein the nucleic acid detection reaction comprises a sequencing-by-ligation reaction.

* * * * *

UNITED STATES PATENT AND TRADEMARK OFFICE
CERTIFICATE OF CORRECTION

PATENT NO. : 10,774,374 B2  
APPLICATION NO. : 15/565637  
DATED : September 15, 2020  
INVENTOR(S) : Jonas Frisen et al.

Page 1 of 1

It is certified that error appears in the above-identified patent and that said Letters Patent is hereby corrected as shown below:

On the Title Page

Item (56) Column 2, Line 3, delete "/datasheet/" and insert -- /datasheets/ --, therefor.

In the Specification

In the Cross-Reference, Column 1, Approximately Line 9, delete "Apr. 6, 2016," and insert -- Apr. 4, 2016, --, therefor.

Signed and Sealed this  
Twenty-sixth Day of January, 2021

Drew Hirshfeld  
*Performing the Functions and Duties of the*  
*Under Secretary of Commerce for Intellectual Property and*  
*Director of the United States Patent and Trademark Office*